(12) United States Patent
Kasai

(10) Patent No.: US 8,432,439 B2
(45) Date of Patent: Apr. 30, 2013

(54) ENDOSCOPE APPARATUS AND METHOD OF INPUTTING CHARACTER STRING

(75) Inventor: Yoichiro Kasai, Tokyo (JP)

(73) Assignee: Olympus Corporation, Tokyo (JP)

( * ) Notice: Subject to any disclaimer, the term of this patent is extended or adjusted under 35 U.S.C. 154(b) by 541 days.

(21) Appl. No.: 12/430,351

(22) Filed: Apr. 27, 2009

(65) Prior Publication Data

US 2009/0268018 A1     Oct. 29, 2009

(30) Foreign Application Priority Data

Apr. 28, 2008  (JP) ................. P2008-117776

(51) Int. Cl.
*H04N 7/18*     (2006.01)
(52) U.S. Cl.
USPC .......................................... 348/65
(58) Field of Classification Search .............. 348/65; 600/109
See application file for complete search history.

(56) References Cited

U.S. PATENT DOCUMENTS

| | | | |
|---|---|---|---|
| 2004/0080541 A1* | 4/2004 | Saiga et al. | 345/805 |
| 2008/0052126 A1 | 2/2008 | Sasai et al. | |
| 2009/0303316 A1* | 12/2009 | Iwasaki et al. | 348/65 |

FOREIGN PATENT DOCUMENTS

| | | |
|---|---|---|
| JP | 06-025934 U | 4/1994 |
| JP | 8-112239 A | 5/1996 |
| JP | 11-312202 A | 11/1999 |
| JP | 2000-259327 A | 9/2000 |
| JP | 2004-348687 A | 12/2004 |
| JP | 2005-110944 A | 4/2005 |
| JP | 2008-052544 A | 3/2008 |

OTHER PUBLICATIONS

Japanese Office Action dated Dec. 11, 2012 (and English translation thereof) in counterpart Japanese Application No. 2008-117776.

* cited by examiner

*Primary Examiner* — Ario Etienne
*Assistant Examiner* — Hee Soo Kim
(74) *Attorney, Agent, or Firm* — Holtz, Holtz, Goodman & Chick, PC

(57) ABSTRACT

An endoscope apparatus including: an endoscope; an image signal processing portion; a display signal generating portion for displaying an image and a character input screen; an operation portion that inputs a character; a character string storage portion that stores a character string and an operation state of the apparatus in a state where the character string is correlated to the operation state; a display instruction detecting portion that detects a display instruction of the character input screen; an operation state detecting portion that detects an operation state of the apparatus; a reading portion that reads a character string, which corresponds to the detected operation state; and a control portion that controls the display signal generating portion to display a screen including a component for selecting the read character string and controls the display signal generating portion to display a character string corresponding to the component.

20 Claims, 20 Drawing Sheets

FIG. 3A

| | |
|---|---|
| R-985-17 | ⎫ |
| R-985-48 | ⎬ CHARACTER STRINGS DISPLAYED ON FIRST PAGE OF CANDIDATE COLUMN |
| R-985-AN1 | ⎭ |
| R1340-6 | ⎫ |
| R1690-42 | ⎬ CHARACTER STRINGS DISPLAYED ON SECOND PAGE OF CANDIDATE COLUMN |
| SATO | ⎭ |
| SUZUKI | ⎫ |
| TANAKA | ⎬ CHARACTER STRINGS DISPLAYED ON THIRD PAGE OF CANDIDATE COLUMN |
| YAMADA | ⎭ |
| ONO | ⎫ |
| OK | ⎬ CHARACTER STRINGS DISPLAYED ON FOURTH PAGE OF CANDIDATE COLUMN |
| NG | ⎭ |
| . | . |
| . | . |
| . | . |
| | |

FIG. 3B

| | |
|---|---|
| COLLISION OF FOREIGN MATTERS | ⎫ |
| CORROSION | ⎬ CHARACTER STRINGS DISPLAYED ON FIRST PAGE OF CANDIDATE COLUMN |
| MANUFACTURE DEFECTS | ⎭ |
| → | ⎫ |
| ← | ⎬ CHARACTER STRINGS DISPLAYED ON SECOND PAGE OF CANDIDATE COLUMN |
| ↑ | |
| ↓ | ⎭ |
| MISSING | ⎫ |
| DEFORMATION | ⎬ CHARACTER STRINGS DISPLAYED ON THIRD PAGE OF CANDIDATE COLUMN |
| OK | ⎭ |
| NG | ⎫ |
| REPLACEMENT OF COMPONENT IS REQUIRED | ⎬ CHARACTER STRINGS DISPLAYED ON FOURTH PAGE OF CANDIDATE COLUMN |
| . | . |
| . | . |
| . | . |
| COLLECTION AND ANALYSES ARE REQUIRED | |

FIG. 16

| | A | B | C |
|---|---|---|---|
| R-985-17 | 3 | 1 | 0 |
| R-985-48 | 2 | 0 | 0 |
| R-985-AN1 | 5 | 0 | 0 |
| R1340-6 | 2 | 1 | 0 |
| R1690-42 | 1 | 0 | 1 |
| SATO | 5 | 1 | 0 |
| SUZUKI | 7 | 3 | 0 |
| TANAKA | 3 | 1 | 0 |
| YAMADA | 5 | 1 | 0 |
| ONO | 2 | 0 | 0 |
| OK | 10 | 1 | 0 |
| NG | 2 | 7 | 0 |
| COLLISION OF FOREIGN MATTERS | 0 | 2 | 0 |
| CORROSION | 0 | 5 | 0 |
| MANUFACTURE DEFECTS | 0 | 3 | 0 |
| → | 0 | 10 | 0 |
| ← | 0 | 8 | 0 |
| ↑ | 0 | 1 | 0 |
| ↓ | 0 | 0 | 0 |
| MISSING | 0 | 10 | 0 |
| DEFORMATION | 0 | 4 | 0 |
| REPLACEMENT OF COMPONENT IS REQUIRED | 0 | 2 | 0 |
| MIYAYASHIKI | 1 | 0 | 0 |
| COLLECTION AND ANALYSES ARE REQUIRED | 0 | 3 | 0 |
| . | 0 | 0 | 0 |
| . | . | . | . |
| . | . | . | . |
| . | . | . | . |
| | 0 | 0 | 0 |
| | 0 | 0 | 0 |
| | 0 | 0 | 0 |

FIG. 17

|  | A | B | C |
|---|---|---|---|
| OK | 10 | 1 | 0 |
| SUZUKI | 7 | 3 | 0 |
| R-985-AN1 | 5 | 0 | 0 |
| SATO | 5 | 1 | 0 |
| YAMADA | 5 | 1 | 0 |
| R-985-17 | 3 | 1 | 0 |
| TANAKA | 3 | 1 | 0 |
| R-985-48 | 2 | 0 | 0 |
| R1340-6 | 2 | 1 | 0 |
| ONO | 2 | 0 | 0 |
| NG | 2 | 7 | 0 |
| R1690-42 | 1 | 0 | 1 |
| MIYAYASHIKI | 1 | 0 | 0 |
| COLLISION OF FOREIGN MATTERS | 0 | 2 | 0 |
| CORROSION | 0 | 5 | 0 |
| MANUFACTURE DEFECTS | 0 | 3 | 0 |
| → | 0 | 10 | 0 |
| ← | 0 | 8 | 0 |
| ↑ | 0 | 1 | 0 |
| ↓ | 0 | 0 | 0 |
| MISSING | 0 | 10 | 0 |
| DEFORMATION | 0 | 4 | 0 |
| REPLACEMENT OF COMPONENT IS REQUIRED | 0 | 2 | 0 |
| COLLECTION AND ANALYSES ARE REQUIRED | 0 | 3 | 0 |
| . | 0 | 0 | 0 |
| . | . | . | . |
| . | . | . | . |
| . | . | . | . |
|  | 0 | 0 | 0 |
|  | 0 | 0 | 0 |
|  | 0 | 0 | 0 |

FIG. 18

| | A | B | C |
|---|---|---|---|
| → | 0 | 10 | 0 |
| MISSING | 0 | 10 | 0 |
| ← | 0 | 8 | 0 |
| NG | 2 | 7 | 0 |
| CORROSION | 0 | 5 | 0 |
| DEFORMATION | 0 | 4 | 0 |
| SUZUKI | 7 | 3 | 0 |
| MANUFACTURE DEFECTS | 0 | 3 | 0 |
| COLLECTION AND ANALYSES ARE REQUIRED | 0 | 3 | 0 |
| COLLISION OF FOREIGN MATTERS | 0 | 2 | 0 |
| REPLACEMENT OF COMPONENT IS REQUIRED | 0 | 2 | 0 |
| OK | 10 | 1 | 0 |
| SATO | 5 | 1 | 0 |
| YAMADA | 5 | 1 | 0 |
| R-985-17 | 3 | 1 | 0 |
| TANAKA | 3 | 1 | 0 |
| R1340-6 | 2 | 1 | 0 |
| ↑ | 0 | 1 | 0 |
| R-985-AN1 | 5 | 0 | 0 |
| R-985-48 | 2 | 0 | 0 |
| ONO | 2 | 0 | 0 |
| R1690-42 | 1 | 0 | 1 |
| MIYAYASHIKI | 1 | 0 | 0 |
| ↓ | 0 | 0 | 0 |
| . | 0 | 0 | 0 |
| . | . | . | . |
| . | . | . | . |
| . | . | . | . |
| | 0 | 0 | 0 |
| | 0 | 0 | 0 |
| | 0 | 0 | 0 |

ENDOSCOPE APPARATUS AND METHOD OF INPUTTING CHARACTER STRING

BACKGROUND OF THE INVENTION

1. Field of the Invention

The present invention relates to an endoscope apparatus capable of inputting a character and a program for controlling the operation thereof.

Priority is claimed on Japanese Patent Application No. 2008-117776 filed on Apr. 28, 2008, the content of which is incorporated herein by reference.

2. Description of Related Art

An example of a method for efficiently performing character input in household apparatuses even when the types or number of keys used for the character input is limited includes a method of providing a character string storage portion that can register character strings and a character string selecting portion that selects and calls a character string from the character strings registered in the character string storage portion (for example, refer to Japanese Unexamined Patent Application, First Publication No. 2000-259327). Also in an industrial endoscope, the types or number of input units is small since the industrial endoscope tends to be made small.

As operation modes of a general industrial endoscope, there are a live mode in which a captured image is displayed in real time, a play mode in which a recorded image is played, and a measurement mode in which the length of a damaged part, the area of a corroded part, and the like of a test subject which is a photographic subject are measured on an acquired image. In the live mode and the measurement mode, an image can be recorded in a recording medium, such as a CF card. In addition, the industrial endoscope has a function of recording character string information relevant to an image as a part of an image file and can adopt the above-described method like household apparatuses in order to input a character string efficiently.

SUMMARY OF THE INVENTION

According to an aspect of the invention, an endoscope apparatus includes: an endoscope that photoelectrically generates an image signal of a subject; an image signal processing portion that processes the image signal to generate image data; a display signal generating portion that generates a display signal for displaying an image based on the image data and a character input screen; an operation portion that inputs a character by operating the character input screen; a character string storage portion that stores a character string and an operation state of the apparatus in a state where the character string is correlated to the operation state of the apparatus; a display instruction detecting portion that detects a display instruction of the character input screen; an operation state detecting portion that detects an operation state of the apparatus; a reading portion that reads a character string, which corresponds to the operation state detected by the operation state detecting portion, from the character string storage portion when the display instruction is detected; and a control portion that controls the display signal generating portion to display a screen including a component for selecting the character string read by the reading portion and, when an operation on the component is detected, controls the display signal generating portion to display a character string corresponding to the component.

Furthermore, according to another aspect of the invention, there is provided a program causing a computer, which controls an endoscope apparatus including an endoscope that generates an image signal of a subject, an image signal processing portion that processes the image signal to generate image data, a display signal generating portion that generates a display signal for displaying an image based on the image data and a character input screen and an operation portion that inputs a character by operating the character input screen, to function as; a character string storage portion that stores a character string and an operation state of the apparatus in a state where the character string is correlated to the operation state of the apparatus; a display instruction detecting portion that detects a display instruction of the character input screen; an operation state detecting portion that detects an operation state of the apparatus; a reading portion that reads a character string, which corresponds to the operation state detected by the operation state detecting portion, from the character string storage portion when the display instruction is detected; and a control portion that controls the display signal generating portion to display a screen including a component for selecting the character string read by the reading portion and, when an operation on the component is detected, controls the display signal generating portion to display a character string corresponding to the component.

BRIEF DESCRIPTION OF THE DRAWINGS

FIGS. 3A and 3B are reference views showing the contents of a favorite list in an embodiment of the invention.

FIG. 16 is a reference view showing the contents of a favorite list in an embodiment of the invention.

FIG. 17 is a reference view showing the contents of a favorite list in an embodiment of the invention.

FIG. 18 is a reference view showing the contents of a favorite list in an embodiment of the invention.

DETAILED DESCRIPTION OF THE INVENTION

Figure 1:
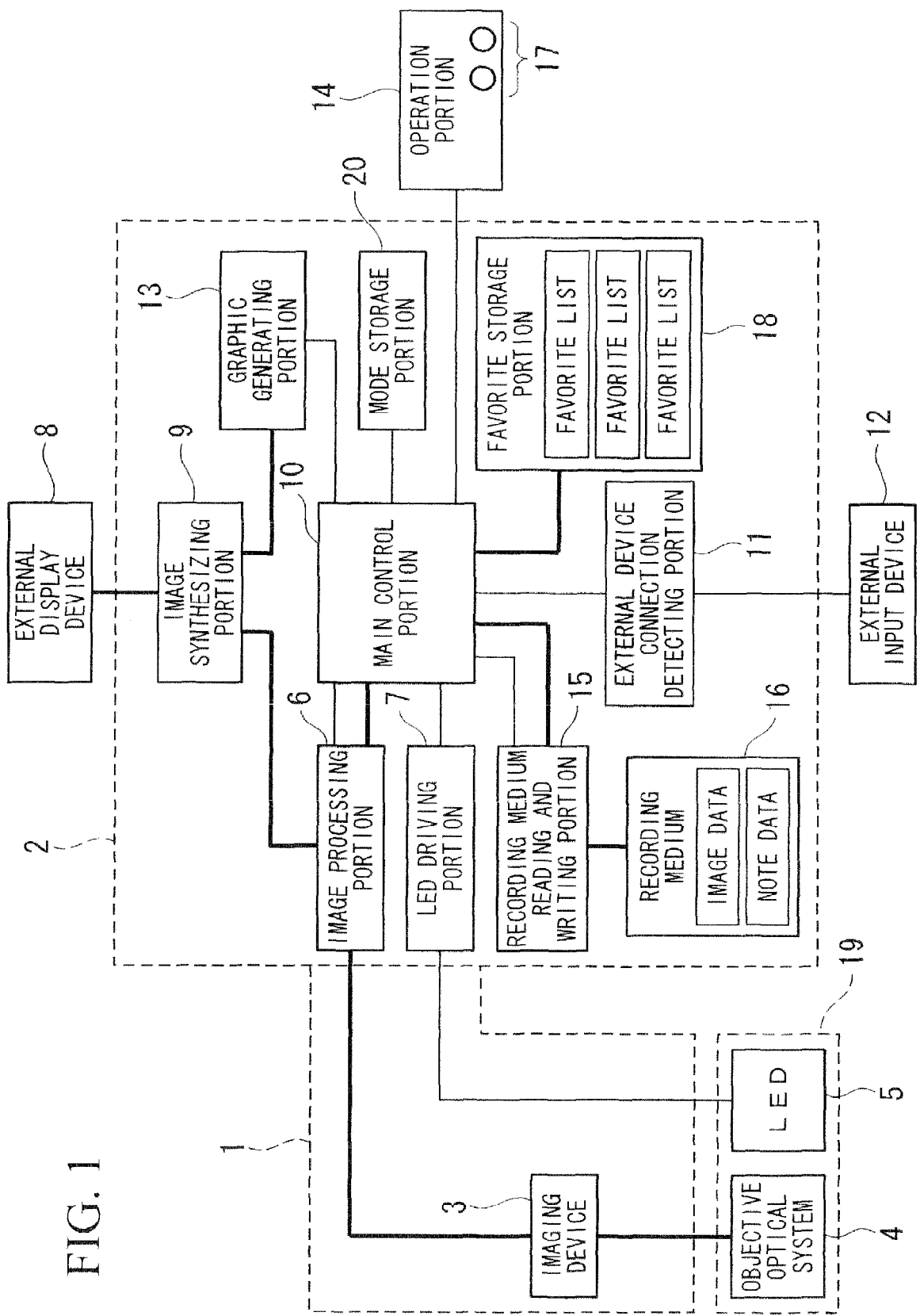
FIG. 1 is a block diagram showing the configuration of an endoscope apparatus according to an embodiment of the invention.

Hereinafter, embodiments of the invention will be described with reference to the accompanying drawings. FIG. 1 shows the configuration of an endoscope apparatus according to an embodiment of the invention. As shown in FIG. 1, an endoscope apparatus includes a narrow and long insertion portion 1, a main body 2 which forms a housing, an external display device 8 such as an LCD, and an operation portion 14 for various operations.

An inspector inserts the insertion portion 1 into a test subject, such as a pipe, accesses a desired test portion while checking an image displayed on the external display device 8, and performs test and diagnostic operations on the basis of the image. A replaceable optical adapter 19 is connected to the tip of the insertion portion 1. The optical adapter 19 has an objective optical system 4 which images light from the test subject and an LED 5 which illuminates the test subject. In addition, an imaging device 3 which photoelectrically converts incident light into an image signal is disposed at the tip of the insertion portion 1. An image of the test subject illuminated by the LED 5 is formed on the imaging device 3 by the objective optical system 4 and is photoelectrically converted into an image signal by the imaging device 3.

The main body 2 has an image processing portion 6, an LED driving portion 7, an image synthesizing portion 9, a main control portion 10, an external device connection detecting portion 11, a graphic generating portion 13, a recording medium reading and writing portion 15, a recording medium 16, a favorite storage portion 18, and a mode storage portion 20. An image signal output from the imaging device 3 is converted into a video signal (image data) and is input to the image processing portion 6. The image processing portion 6 performs processing, such as gamma correction processing, edge reinforcement processing, digital zoom processing, and the like on the video signal in order to generate an image through which the test subject that is a photographic subject can be observed.

The graphic generating portion 13 generates a graphic image signal for graphic user interface (hereinafter, referred to as a 'GUI'), such as a menu display. The image synthesizing portion 9 synthesizes the video signal processed by the image processing portion 6 with the graphic image signal generated by the graphic generating portion 13 so as to generate a display signal for displaying an image of the test subject imaged by the imaging device 3, a character input screen, and the like. The display signal is output to the external display device 8 and the image of the test subject, the character input screen, and the like are displayed by the external display device 8.

The LED driving portion 7 drives the LED 5 in the optical adapter 19. The external device connection detecting portion 11 detects a connection state of an external input device 12 (for example, a keyboard) which can be connected to the main body 2 or removed from the main body 2. The operation portion 14 is an input device for performing various kinds of input by a screen operation using a GUI. In addition, the operation portion 14 has a screen start switch 17 for starting a character input screen. A menu operation or character input is performed by operation of the operation portion 14 or the external input device 12.

The main control portion 10 controls each portion in the endoscope apparatus by executing a program stored in a nonvolatile memory (not shown). Particularly for the character input, the main control portion 10 controls the graphic generating portion 13 on the basis of the content of a user's operation of the operation portion 14 or the external input device 12. Then, a result of the character input is displayed on the external display device 8. A character string generated as a result of the character input is stored in a memory (not shown) in the main control portion 10.

Moreover, for recording of an image, the main control portion 10 controls the recording medium reading and writing portion 15. The recording medium reading and writing portion 15 writes and records image data output from the image processing portion 6 in the recording medium 16 according to the control of the main control portion 10. At this time, the character string stored in the memory (not shown) in the main control portion 10 is also stored as a part of image data.

The recording medium 16 is a recording medium built in the endoscope apparatus or an external recording medium which can be connected to the main body 2 or removed from the main body 2. List type note data including a category and contents may be stored together with the image data in the recording medium 16. Details of the note data will be described later.

The favorite storage portion 18 stores a character string (favorite) that the user registered in advance by a predetermined operation. The registered character string is stored in the favorite storage portion 18 as a favorite list in which a plurality of character strings are listed. The character string may be one word or may include a plurality of words. In addition, the character string may include a figure, a symbol, and the like. The number of favorite lists stored in the favorite storage portion 18 or the number of character strings in a favorite list is not particularly limited.

The mode storage portion 20 stores an operation mode (operation state) of a current apparatus. At the time of switching of an operation mode, the main control portion 10 updates mode information stored in the mode storage portion 20. Examples of the operation mode according to the present embodiment include a live mode in which a captured image is displayed in real time, a play mode in which a recorded image is played, and a measurement mode in which the length of a damaged part, the area of a corroded part, and the like of a test subject which is a photographic subject are measured on an acquired image.

Each operation mode is switched by operation of a button provided in the operation portion 14. When the main control portion 10 detects pressing of a live button, the operation mode switches to the live mode. In this case, the main control portion 10 updates the mode information stored in the mode storage portion 20 to the live mode. Then, when the main control portion 10 detects pressing of a freeze button, the main control portion 10 acquires image data from the image processing portion 6.

When the main control portion 10 detects pressing of a measurement start button in a state where the main control portion 10 acquires image data, the operation mode switches to the measurement mode. In this case, the main control portion 10 updates the mode information stored in the mode storage portion 20 to the measurement mode. Moreover, when the main control portion 10 detects pressing of an image play button, the operation mode switches to the play mode. In this case, the main control portion 10 updates the mode information stored in the mode storage portion 20 to the play mode. In addition, when the main control portion 10 detects pressing of a record button in a state where the operation mode is the live mode or the measurement mode, image data can be recorded in the recording medium 16. Furthermore, there is an operation mode in which note data is edited in addition to the above operation modes.

In the endoscope apparatus, the type of character string to be added to an image changes for every operation mode described above. For example, in the live mode, character strings, such as an inspector name (for example, 'SATO'), a test subject name (for example, 'R-985-17' indicating the engine of an aircraft), a test portion name (for example, 'AP-1' indicating an access port name of an engine), and a test result (for example, 'OK' or 'NG'), are mainly input. Moreover, in the measurement mode, an arrow character (for example, '→') for highlighting an observed portion or a character string unique to a measurement function are mainly input. Moreover, in the play mode, character input for changing an error of a character string which has been already recorded is mainly performed, and so a character string to be input changes according to whether or not a measurement result is added to a target image, as described above.

Next, an operation regarding character input of the endoscope apparatus according to the present embodiment will be described. At the time of character input, the main control portion 10 detects the content of a user's operation of the operation portion 14 or the external input device 12 on the basis of a signal output from the operation portion 14 or the external input device 12, and controls operation according to the operation content. Hereinbelow, an operation based on the operation content of the operation portion 14 will be described.

First, a first operation example will be described. In the first operation example, a favorite list is prepared for every operation mode and a favorite list corresponding to an operation mode running at the time of character input is used for character input. FIGS. 3A and 3B show the contents of a favorite list in the first operation example. FIG. 3A shows the contents of a favorite list for the live mode, and FIG. 3B shows the contents of a favorite list for the measurement mode. As shown in FIG. 3A, character strings, such as an inspector name, a test subject name, and a test result, are registered in the favorite list for the live mode.

Moreover, as shown in FIG. 3B, character strings, such as arrow characters, are registered into the favorite list for the measurement mode. A place, in which a character string is not registered, in the favorite list is a blank. In addition, although not shown, a favorite list for the play mode is also prepared.

In FIGS. 3A and 3B, one page on which character strings can be simultaneously displayed in a character input screen are set in the unit of three lines from the head of the favorite list. That is, character strings from the head (first line) of the favorite list to a third line are set as a first page, character strings from a fourth line to a sixth line are set as a second page, and subsequent pages are similarly set in the unit of three lines. The character strings on the first page are displayed at the start of the character input screen. Then, the displayed character strings can be switched for every page.

Figure 4A:
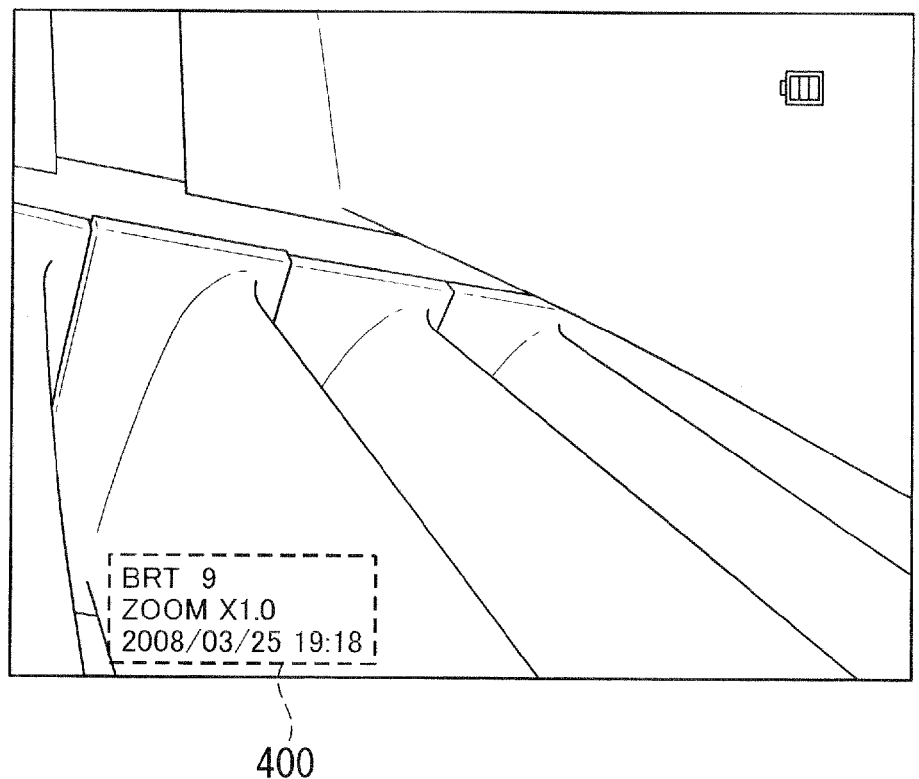
FIGS. 4A and 4B are reference views showing screens before character input in an embodiment of the invention.
Figure 4B:
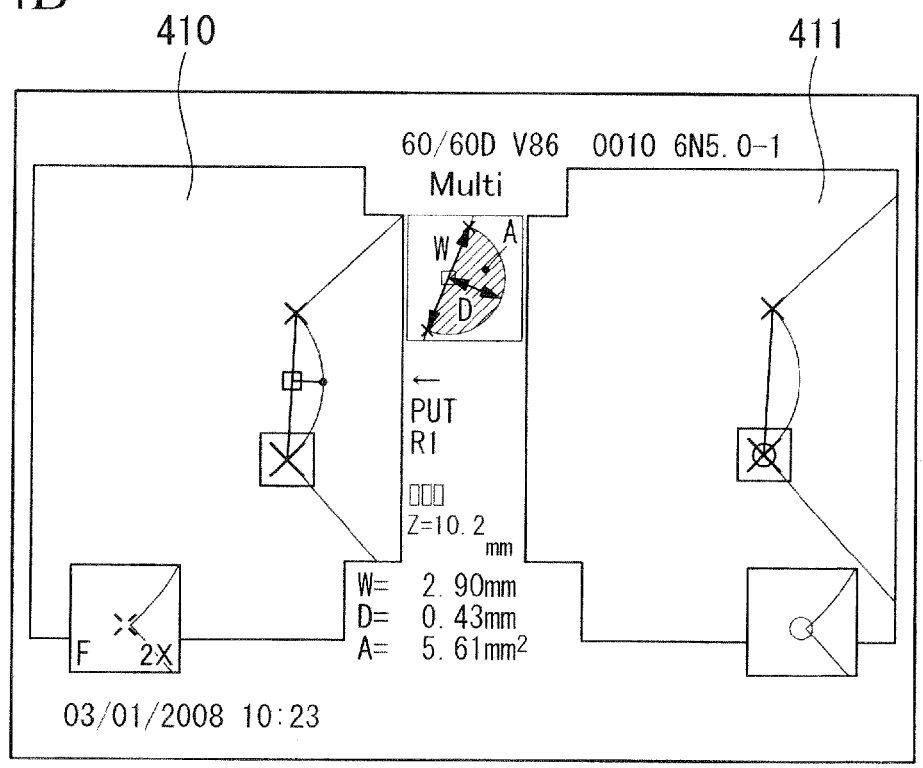

In the case of performing character input, the user starts a character input screen. FIGS. 4A and 4B show a screen of the external display device 8 before a character input screen starts. FIG. 4A shows a screen of the external display device 8 in the live mode. On an image of a test subject based on a video signal processed by the image processing portion 6, a character string 400 based on a graphic image signal generated by the graphic generating portion 13 is displayed. The character string 400 shows an imaging condition, date and time, and the like.

FIG. 4B shows a screen of the external display device 8 in the measurement mode. Images 410 and 411 of the test subject based on the video signal processed by the image processing portion 6 are displayed in two left and right places. These images 410 and 411 are images when a stereo optical adapter that forms two left and right fields of view is used as the optical adapter 19. In addition, various character strings or icons, such as a cursor based on a graphic image signal generated by the graphic generating portion 13, are displayed.

Figure 2:
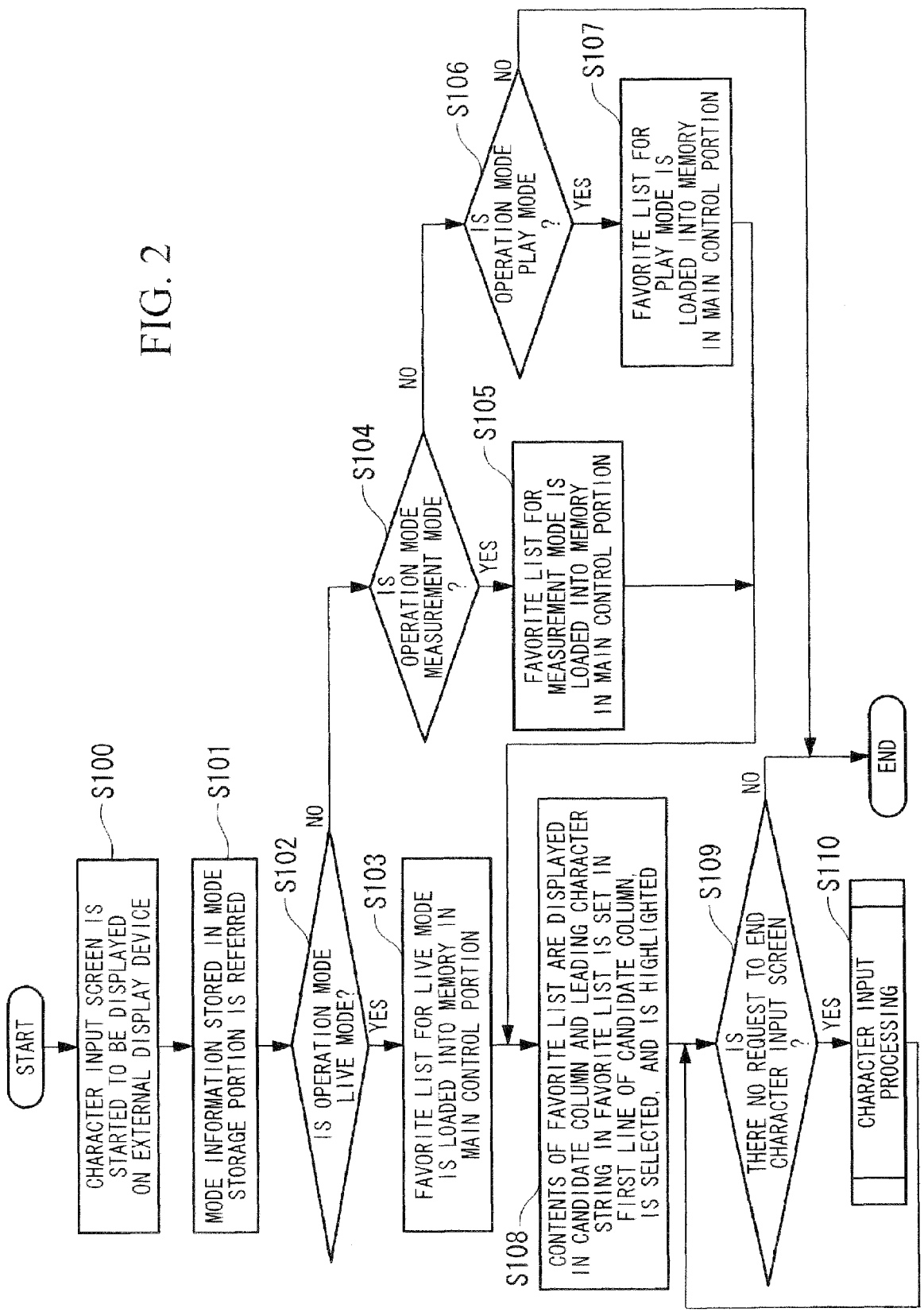
FIG. 2 is a flow chart showing the procedure of an operation of an endoscope apparatus according to an embodiment of the invention.

In the case of performing character input, the user operates the operation portion 14 to input a start instruction (display instruction) of a character input screen. The main control portion 10 detects the start instruction on the basis of a signal output from the operation portion 14. Subsequently, the main control portion 10 executes a control operation regarding character input according to the procedure shown in FIG. 2.

The main control portion 10 that has detected the start instruction instructs the graphic generating portion 13 to display the character input screen. The graphic generating portion 13 generates a graphic image signal for displaying the character input screen and outputs the graphic image signal to the image synthesizing portion 9. The image synthesizing portion 9 outputs the graphic image signal output from the graphic generating portion 13 to the external display device 8. The external display device 8 displays the character input screen on the basis of the graphic image signal (step S100).

Then, the main control portion 10 reads and refers to mode information stored in the mode storage portion 20 (step S101). When the mode information indicates the live mode (in the case of YES in step S102), the main control portion 10 reads a favorite list for the live mode from the favorite storage portion 18 and loads the favorite list for the live mode into a memory in the main control portion 10 (step S103). In addition, when the mode information indicates not the live mode but the measurement mode (in the case of NO in step S102 and YES in step S104), the main control portion 10 reads a favorite list for the measurement mode from the favorite storage portion 18 and loads the favorite list for the measurement mode into the memory in the main control portion 10 (step S105).

In addition, when the mode information indicates not the live mode and not the measurement mode but the play mode (in the case of NO in steps S102 and S104 and YES in step S106), the main control portion 10 reads a favorite list for the play mode from the favorite storage portion 18 and loads the favorite list for the play mode into the memory in the main control portion 10 (step S107). In addition, when the operation mode indicated by the mode information is none of the live mode, the measurement mode, and the play mode (in the case of NO in steps S102, S104, and S106), the control regarding the character input is ended. Subsequent to steps S103, S105, and S107, the main control portion 10 controls the graphic generating portion 13 to generate a graphic image signal for displaying a character input screen including the character string in the favorite list loaded into the memory (step S108).

Figure 5A:
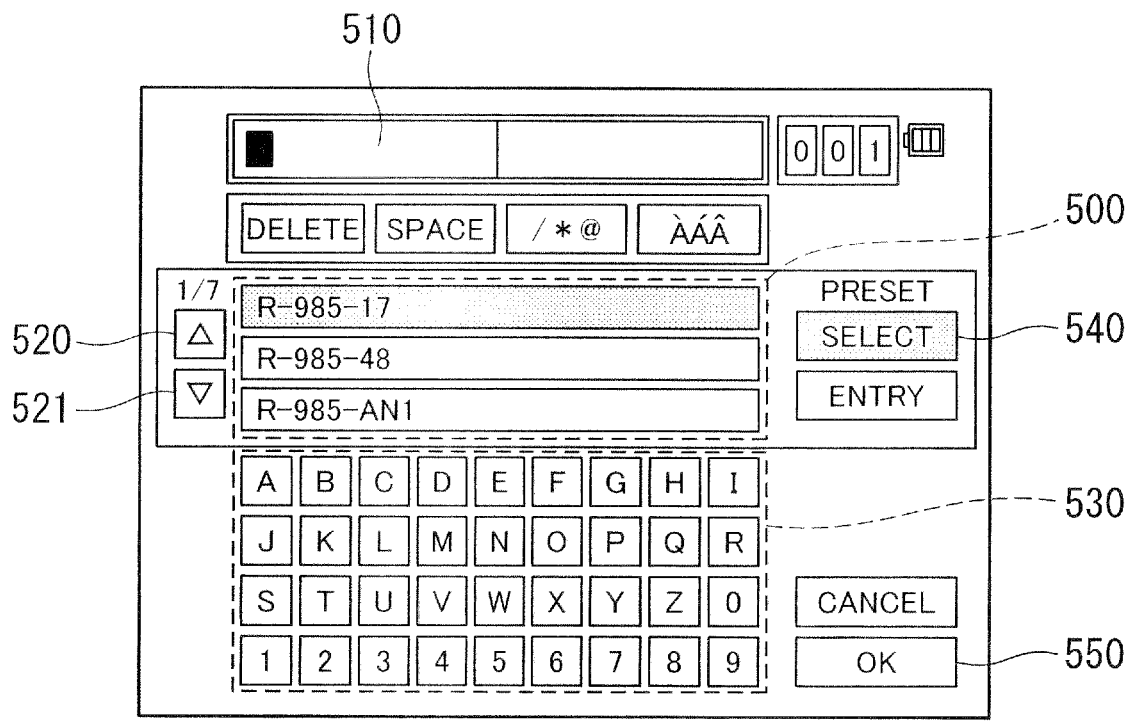
FIGS. 5A and 5B are reference views showing screens at the time of character input (live mode) in an embodiment of the invention.
Figure 5B:
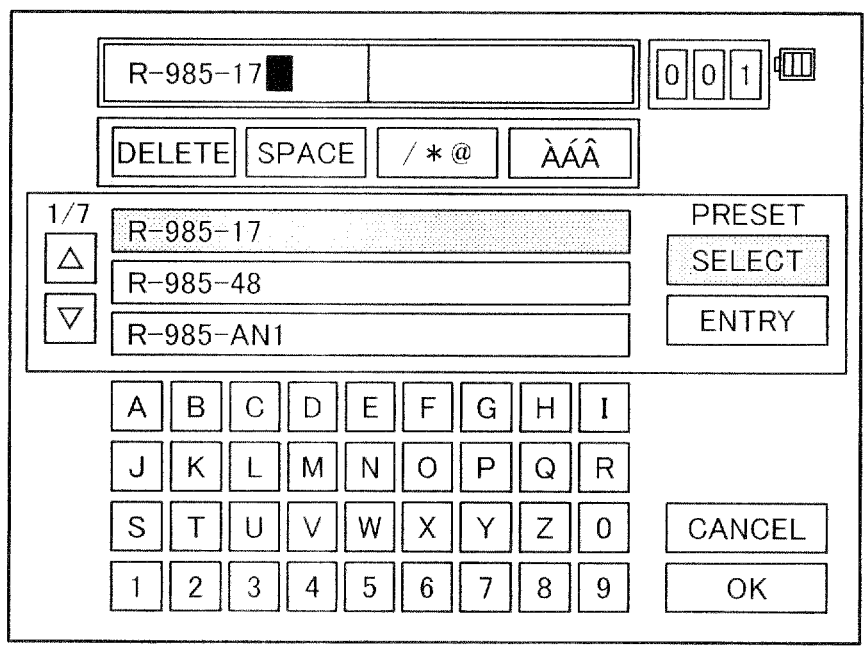
Figure 6A:
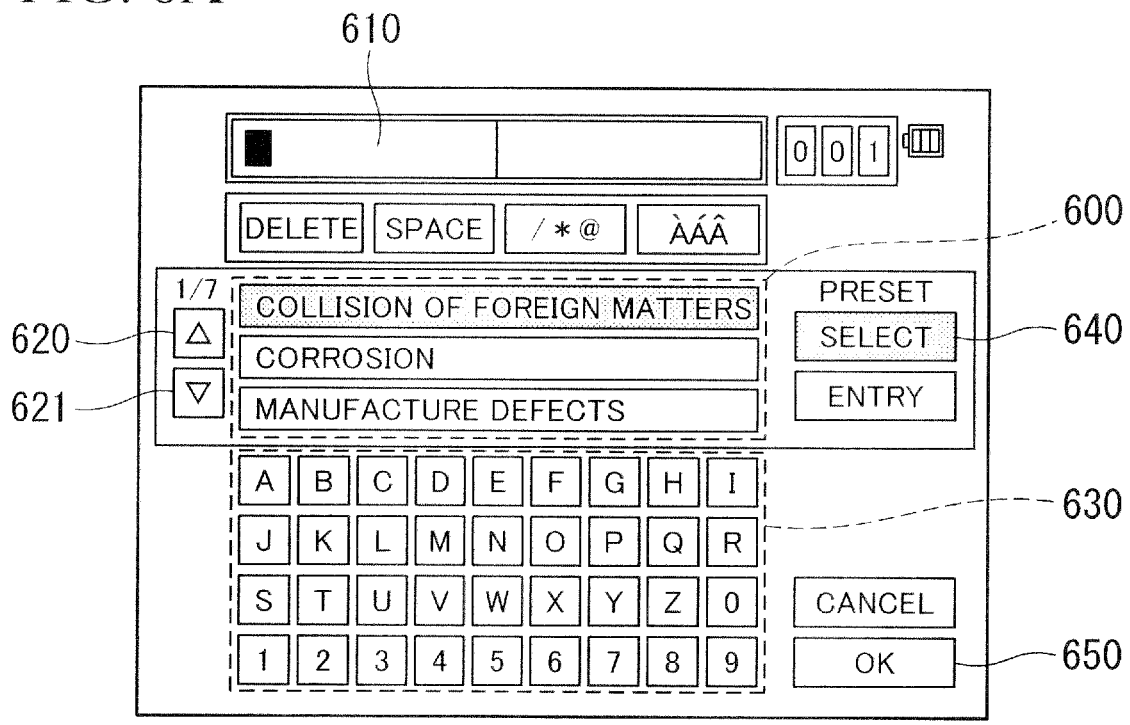
FIGS. 6A and 6B are reference views showing screens at the time of character input (measurement mode) in an embodiment of the invention.
Figure 6B:
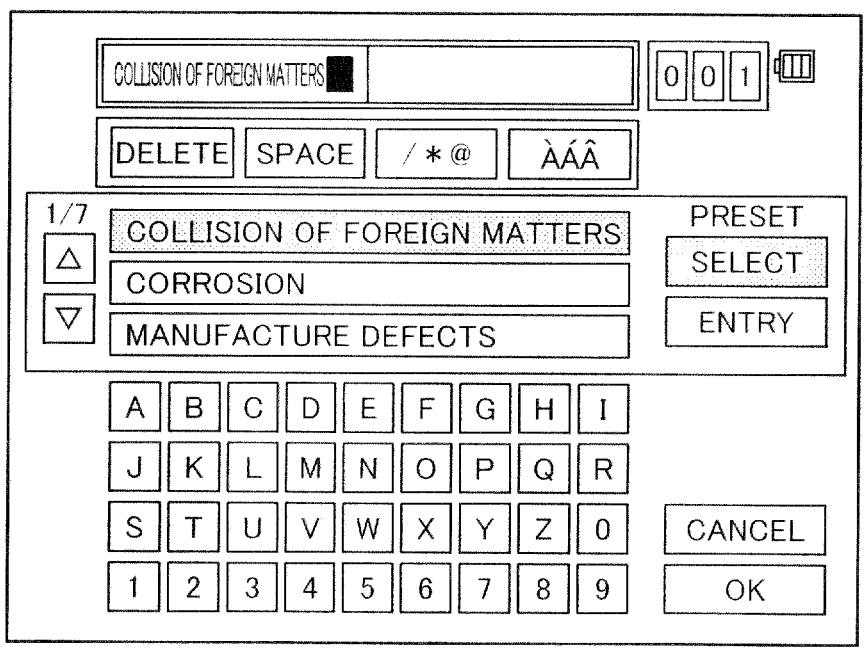

FIGS. 5A and 5B show a screen of the external display device 8 when a character input screen starts in the live mode. In addition, FIGS. 6A and 6B show a screen of the external display device 8 when a character input screen starts in the measurement mode. Buttons and the like, which are GUI components for performing character input, are displayed on the screen. The language displayed on the character input screen is not particularly limited (the same hereinbelow). Character strings in the favorite list are displayed on candidate columns 500 and 600 (FIGS. 5A and 6A). Particularly in a first line of each of the candidate columns 500 and 600, a leading character string in the favorite list is displayed and this character string is selected. When a user instructs input of a character string by operation of the operation portion 14 in a state where a line, in which a desired character string is displayed, of each of the candidate columns 500 and 600 is selected, this character string is displayed on the input each of columns 510 and 610 (FIGS. 5B and 6B). A character string or an icon indicating a type of the operation mode at the start of the character input screen may be displayed on the character input screen.

Subsequent to step S108, the main control portion 10 determines whether or not there is a request to end the character input screen on the basis of a signal output from the operation portion 14 (step S109). If there is no end request (YES in step S109), the main control portion 10 executes character input processing (step S110). In addition, when there is an end request (NO in step S109), the main control portion 10 makes the character input screen not displayed, controls the graphic generating portion 13 to display the fixed character string, and ends the control regarding the character input.

Hereinafter, details of character input processing of step S110 will be described. As shown in FIGS. 5A and 6A, character strings in the favorite list are displayed on the candidate columns 500 and 600. Character strings on the first page in the favorite list are displayed at the start of the character input screen. Displayed character strings may be changed in units of page by operation of previous candidate buttons 520 and 620 and next candidate buttons 521 and 621. Character strings on a previous page is displayed when the previous candidate buttons 520 and 620 have been operated, and character strings on a next page is displayed when the next candidate buttons 521 and 621 have been operated.

The user selects a candidate column, in which a character string that the user wants to input is displayed, and performs an operation of instructing input of the character string by operation of the operation portion 14. When this operation is performed, the main control portion 10 controls the graphic generating portion 13 to display the selected character string on the input columns 510 and 610. By repeating the above operation, the user can input character strings in which character strings in the favorite list are combined.

Figure 7:
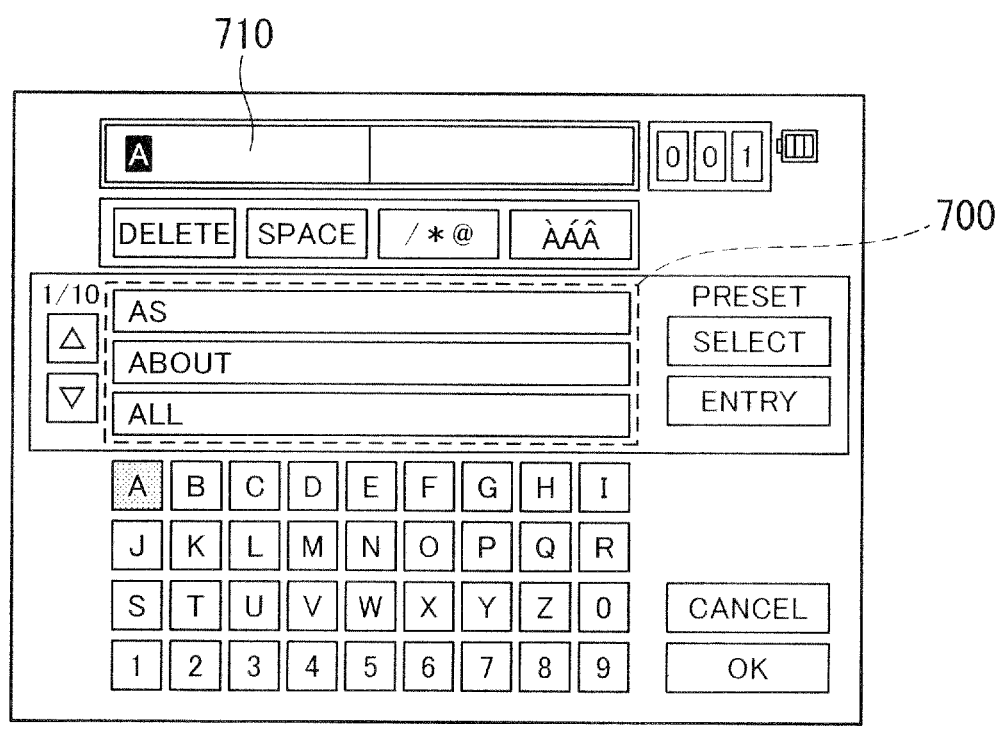
FIG. 7 is a reference view showing a screen at the time of character input (when character buttons are used) in an embodiment of the invention.

In the present embodiment, it is possible to perform both character input using a favorite list and character input using character buttons. When the character input screen starts, the character buttons 530 and 630 which are GUI components for selecting a character are displayed. In the case of performing character input using the character buttons 530 and 630, the user selects a button, on which a character that the user wants to input is displayed, and performs an operation of instructing the input of the character by operation of the operation portion 14. When this operation is performed, the main control portion 10 reads a word dictionary from a storage portion (not shown) and searches a plurality of candidates for character conversion corresponding to the selected character. The main control portion 10 controls the graphic generating portion 13 to display the plurality of searched candidates on a candidate column 700 as shown in FIG. 7.

The user selects a character string that the user wants to input from candidates of character strings displayed on the candidate column 700 and performs an operation of instructing input of the character string by operation of the operation portion 14. When this operation is performed, the main control portion 10 controls the graphic generating portion 13 to display the selected character string on the input column 710. By repeating the above operation, the user can input character strings in which character strings in the favorite list are combined.

Switching between the character input using a favorite list and the character input using character buttons is performed as follows. In the case of performing the character input using character buttons after performing the character input using a favorite list, the user select a character button, on which a character that the user want to input is displayed, by operation of the operation portion 14. Then, the character input using character buttons can be performed in the same manner as described above.

Moreover, in the case of performing the character input using a favorite list after performing the character input using character buttons, the user operate favorite calling buttons 540 and 640 by operation of the operation portion 14. Then, the character input using a favorite list can be performed in the same manner as described above. When the character input using a favorite list and the character input using character buttons are performed continuously, the main control portion 10 controls the graphic generating portion 13 such that a character string in the favorite list and a converted character string using the word dictionary are displayed in combination.

Figure 8A:
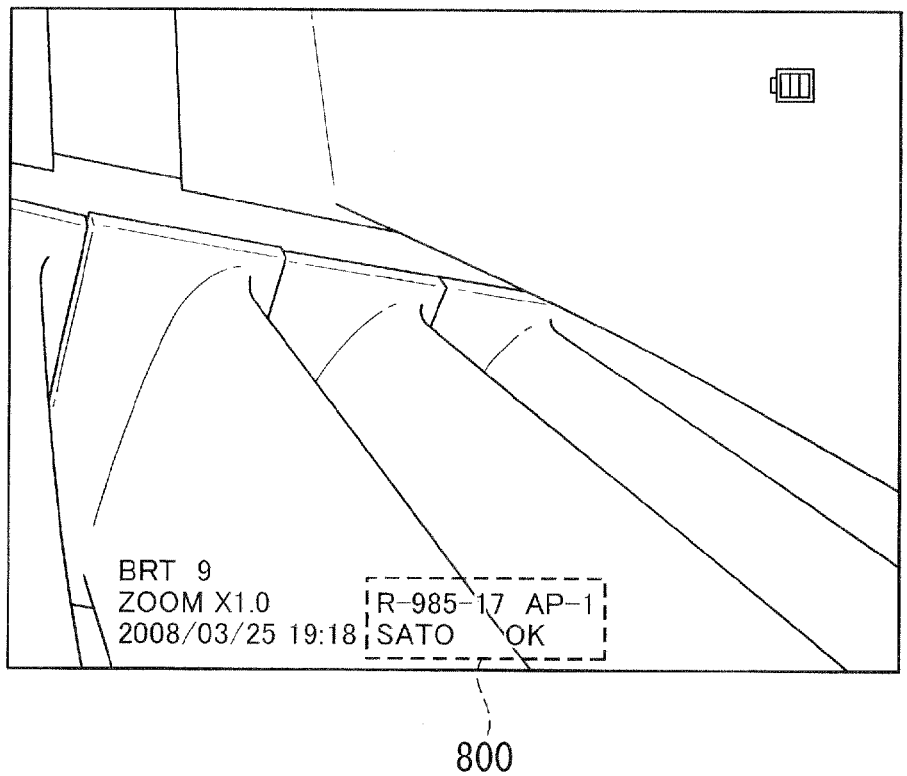
FIGS. 8A and 8B are reference views showing screens after character input in an embodiment of the invention.
Figure 8B:
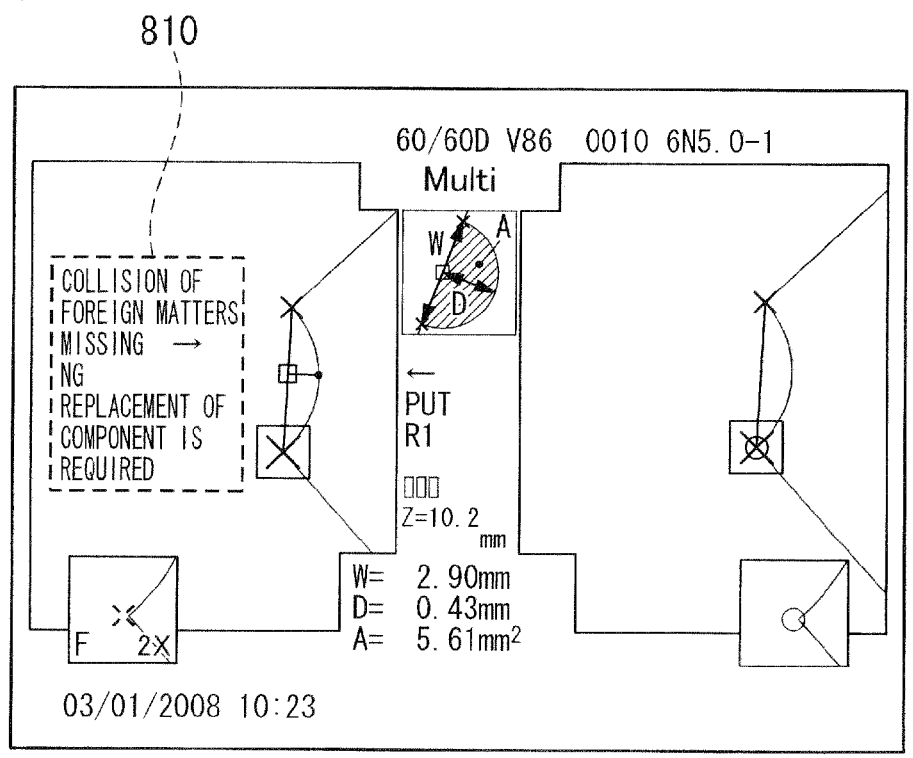

When the user operates decision buttons 550 and 650 by operation of the operation portion 14, the input character string is fixed. When the operation of the decision buttons 550 and 650 is detected, the main control portion 10 ends the character input screen and controls the image processing portion 6, the image synthesizing portion 9, and the graphic generating portion 13 to make the fixed character string overlap the original image. When the character input screen starts in the live mode, the screen at the time of the live mode before the character input screen starts is displayed again and a fixed character string 800 is displayed to overlap the screen as shown in FIG. 8A. Moreover, when the character input screen starts in the measurement mode, the screen at the time of the measurement mode before the character input screen starts is displayed again and a fixed character string 810 is displayed to overlap the screen as shown in FIG. 8B. The character string fixed as described above is stored in a memory (not shown) in the main control portion 10.

Then, when the user inputs an instruction to record the image by operation of the operation portion 14, the main control portion 10 starts an image recording control. The main control portion 10 adds the character string stored in the memory (not shown) to image data output from the image processing portion 6 and outputs the result to the recording medium reading and writing portion 15. The recording medium reading and writing portion 15 writes and records the image data, to which the character string is added, in the recording medium 16.

In the case of performing character input using character buttons, the user needs to operate the character buttons and then select a desired character string from the list of character strings displayed. However, in the case of performing character input using a favorite list, it is sufficient only to select a desired character string from the list of character strings that are automatically displayed. Therefore, an operation required for character input can be reduced. In addition, in the case of performing character input using a favorite list, the favorite list changes according to the operation mode at the start of the character input screen. Accordingly, since it becomes possible to input a favorite list which is optimal in each operation mode, an operation required for character input can be further reduced.

Next, a second operation example will be described. In the second operation example, a character string selected from character strings registered in note data by the user is recorded as a part of image data. The note data is data having a category and contents corresponding to the category as a pair. The user can perform registration and editing of a character string for a category and contents by the same character input manner as in the first operation example. In a category, character strings indicating a large group, such as where and who, are input in many cases. In contents, specific character strings, such as 'NEW YORK', 'LONDON', 'TOKYO', 'SATO', and 'SUZUKI', are input in many cases. The created note data are recorded in the recording medium 16 as a part of image data.

In the second operation example, a favorite list for category input and a favorite list for contents input are prepared, and a favorite list corresponding to the category or contents to which characters are to be input is used when inputting characters in the category or contents. In the case of editing note data, the user operates the operation portion 14 to input a start instruction (display instruction) of a note edit screen. The main control portion 10 detects the start instruction of the note edit screen on the basis of a signal output from the operation portion 14.

The main control portion 10 that has detected the start instruction of the note edit screen instructs the graphic generating portion 13 to display the note edit screen. In this case, the main control portion 10 controls the recording medium reading and writing portion 15 to read note data from the recording medium 16 and controls the graphic generating portion 13 to display a character string of the category and contents included in the note data. The graphic generating portion 13 generates a graphic image signal for displaying the note edit screen and outputs the note edit screen to the image synthesizing portion 9. The image synthesizing portion 9 outputs the graphic image signal output from the graphic generating portion 13 to the external display device 8. The external display device 8 displays the note edit screen on the basis of the graphic image signal.

Figure 10:
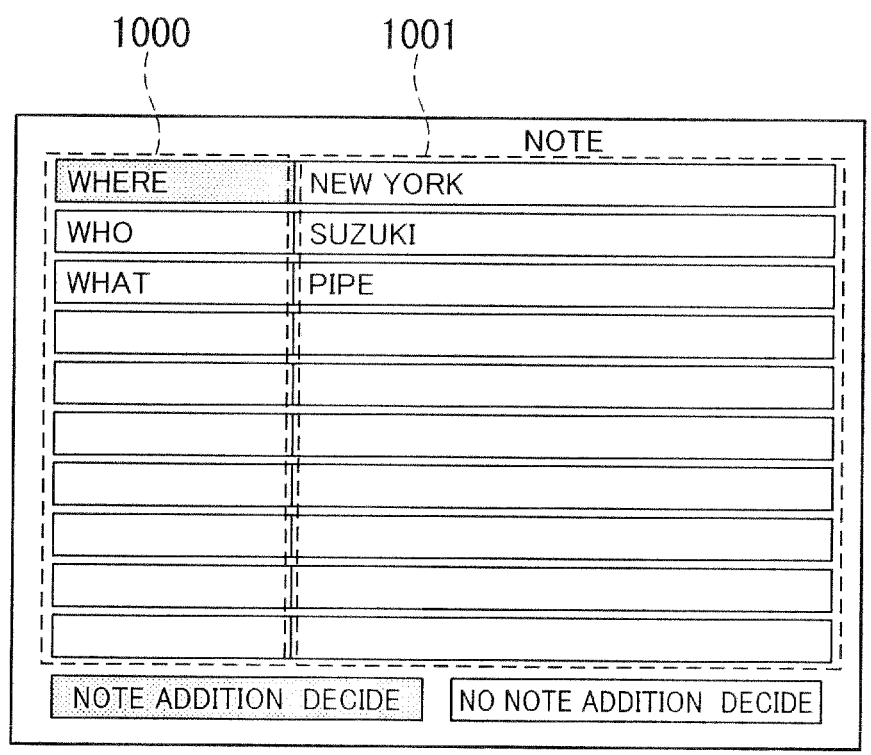
FIG. 10 is a reference view showing a screen before editing note data in an embodiment of the invention.

FIG. 10 shows a screen of the external display device 8 when a note edit screen starts. As shown in FIG. 10, a character string of a category registered in note data is displayed in a list form in a category column 1000. A character string of contents corresponding to a selected category among character strings of contents registered in the note data is displayed in a list form in a contents column 1001. In FIG. 10, the contents 'NEW YORK', 'SUZUKI', and 'PIPE' corresponding to the category 'WHERE' are displayed in the contents column 1001. A blank is displayed when a character string is not registered.

Figure 9:
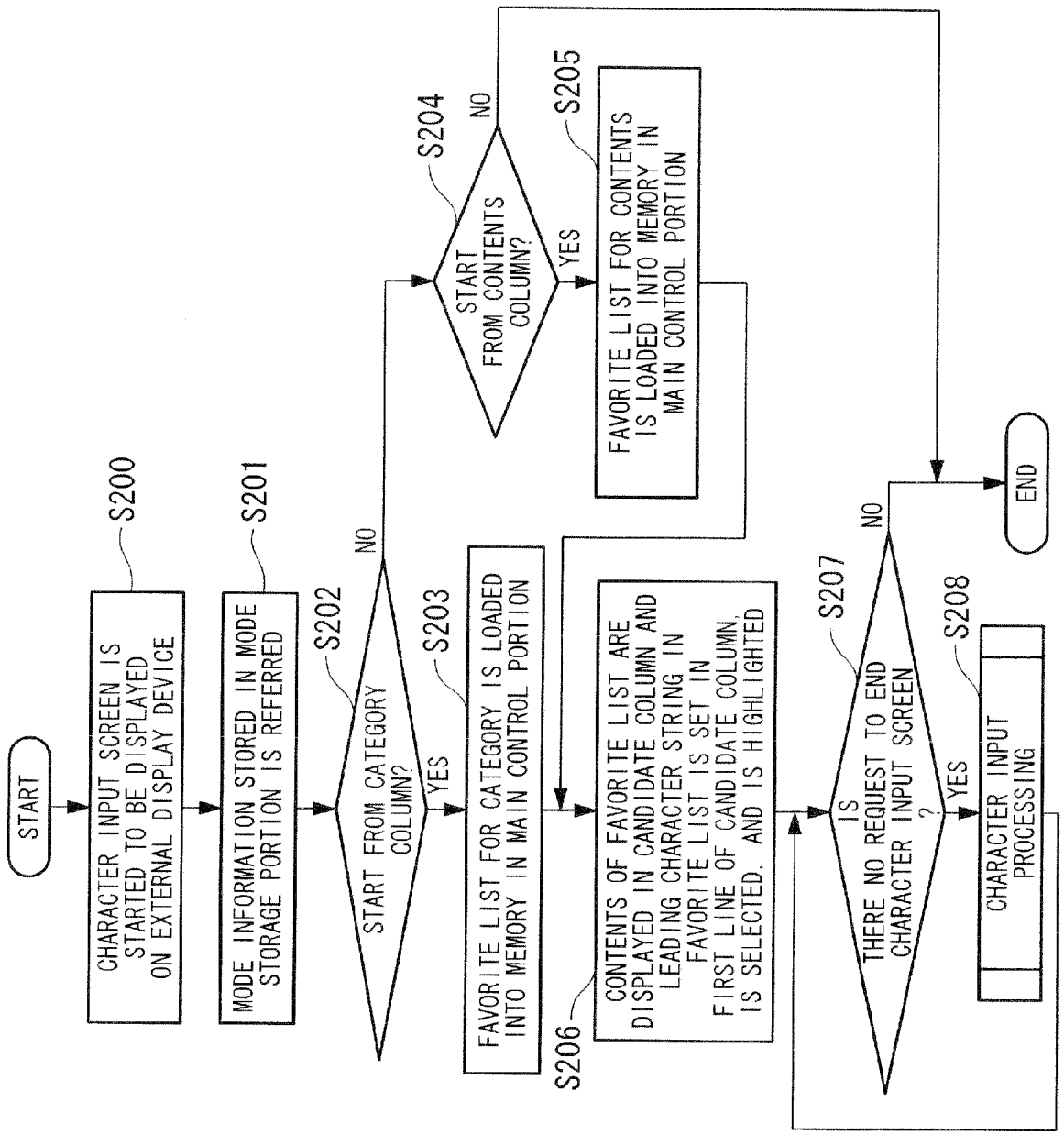
FIG. 9 is a flow chart showing the procedure of an operation of an endoscope apparatus according to an embodiment of the invention.

When inputting a character string in the category column or the contents column, the user selects the category column or the contents column and inputs a start instruction (display instruction) of a character input screen by operation of the operation portion 14. The main control portion 10 detects the start instruction on the basis of a signal output from the operation portion 14. Subsequently, the main control portion 10 executes a control operation regarding character input according to the procedure shown in FIG. 9.

The main control portion 10 that has detected the start instruction instructs the graphic generating portion 13 to display the character input screen. The graphic generating portion 13 generates a graphic image signal for displaying the character input screen and outputs the graphic image signal to the image synthesizing portion 9. The image synthesizing portion 9 outputs the graphic image signal output from the graphic generating portion 13 to the external display device 8.

The external display device 8 displays a character input screen on the basis of the graphic image signal (step S200).

Then, the main control portion 10 reads and refers to mode information stored in the mode storage portion 20 (step S201). The mode information in the second operation example indicates which one of the category column and the contents column is selected. The main control portion 10 updates the mode information according to the selection condition of the category column and the contents column. When the mode information indicates the category column (in the case of YES in step S202), the main control portion reads a favorite list for category input from the favorite storage portion 18 and loads the favorite list for category input into a memory in the main control portion 10 (step S203).

In addition, when the mode information indicates not the category column but the contents column (in the case of NO in step S202 and YES in step S204), the main control portion 10 reads a favorite list for contents input from the favorite storage portion 18 and loads the favorite list for contents input into the memory in the main control portion 10 (step S205). In addition, when the mode information indicates neither the category column nor the contents column (in the case of NO in steps S202 and S204), the control regarding the character input is ended. Subsequent to steps S203 and S205, the main control portion 10 controls the graphic generating portion 13 to generate a graphic image signal for displaying a character input screen including the character string in the favorite list loaded into the memory (step S206).

Figure 11A:
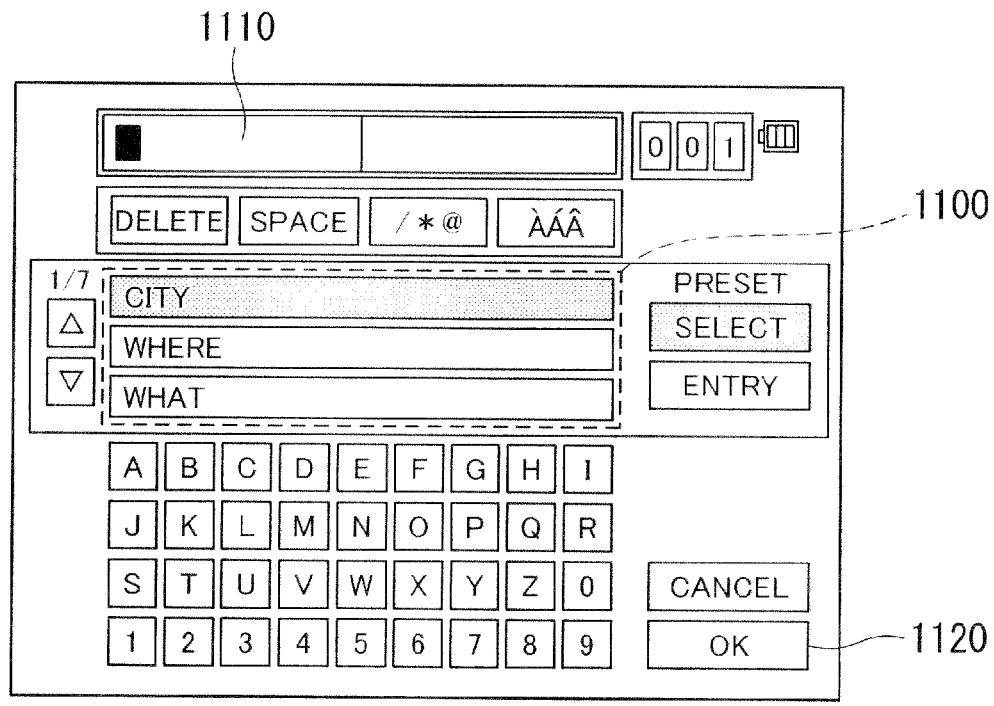
FIGS. 11A and 11B are reference views showing screens at the time of character input (at the time of category input) in an embodiment of the invention.
Figure 11B:
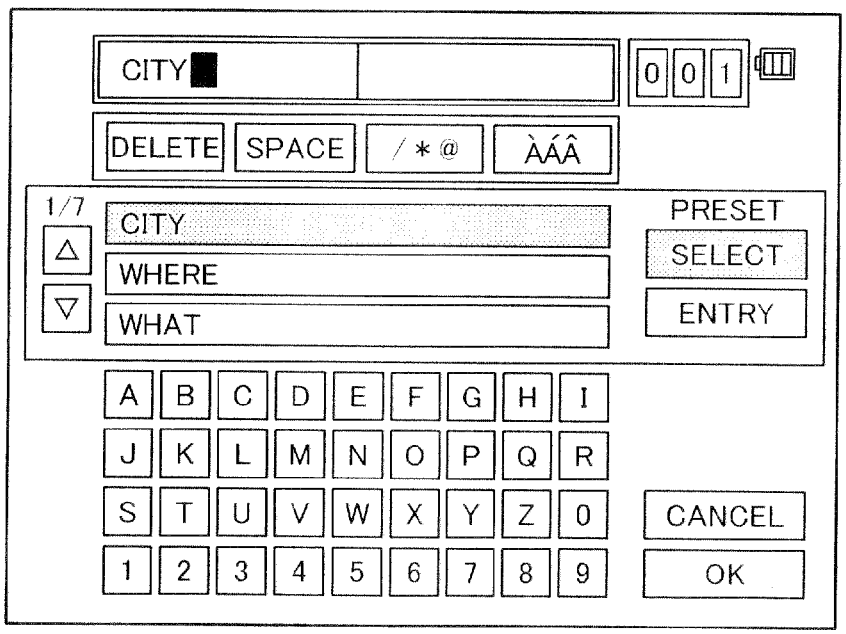
Figure 12A:
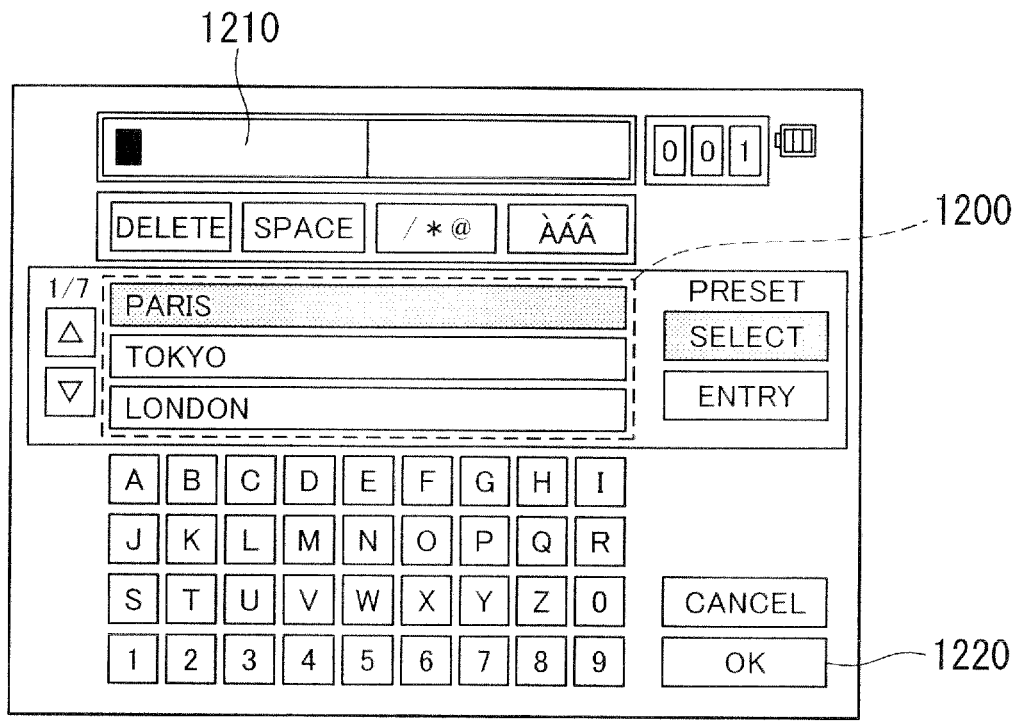
FIGS. 12A and 12B are reference views showing screens at the time of character input (at the time of contents input) in an embodiment of the invention.
Figure 12B:
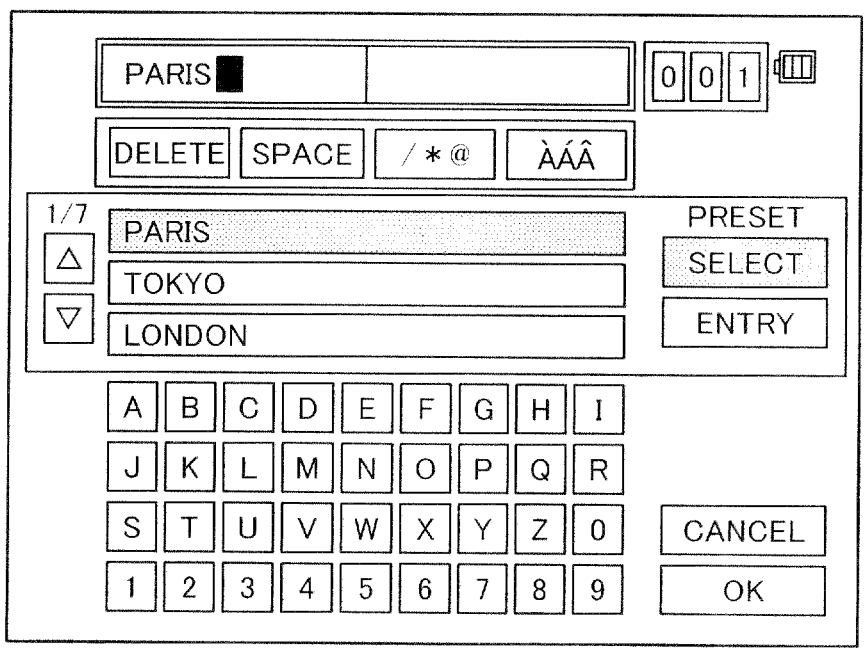

FIGS. 11A and 11B show a screen of the external display device 8 when a character input screen starts from a category column. In addition, FIGS. 12A and 12B show a screen of the external display device 8 when a character input screen starts from a contents column. Buttons and the like, which are GUI components for performing character input, are displayed on a screen. Character strings in a favorite list is displayed on candidate columns 1100 and 1200 (FIGS. 11A and 12A). Particularly in a first line of each of the candidate columns 1100 and 1200, a leading character string in the favorite list is displayed and the character string is selected. When the user instructs input of a character string by operation of the operation portion 14 in a state where a line, in which a desired character string is displayed, of each of the candidate columns 1100 and 1200 is selected, this character string is displayed on the input columns 110 and 1210 (FIGS. 11B and 12B). In addition, a character string or an icon indicating which one of a category column and a contents column is selected at the start of the character input screen may be displayed on the character input screen.

Subsequent to step S206, the main control portion 10 determines whether or not there is a request to end the character input screen on the basis of a signal output from the operation portion 14 (step S207). If there is no end request (YES in step S207), the main control portion 10 executes character input processing (step S208). In addition, when there is an end request (NO in step S207), the main control portion 10 makes the character input screen not displayed, controls the graphic generating portion 13 to display the fixed character string, and ends the control regarding the character input.

Details of the character input processing in step S208 are the same as those in the first operation example. When the user operates decision buttons 1120 and 1220 after performing desired character input by operation of the operation portion 14, the input character string is fixed. When the operation of the decision buttons 1120 and 1220 is detected, the main control portion 10 ends the character input screen and controls the graphic generating portion 13 to display the fixed character string on the note edit screen.

Figure 13A:
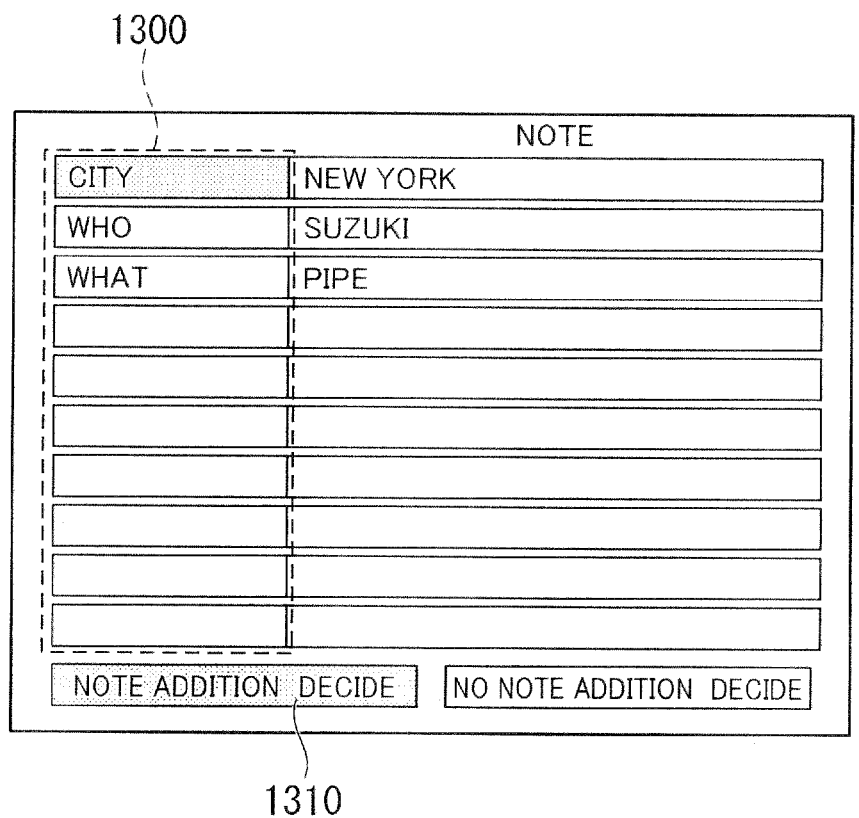
FIGS. 13A and 13B are reference views showing screens after editing note data in an embodiment of the invention.
Figure 13B:
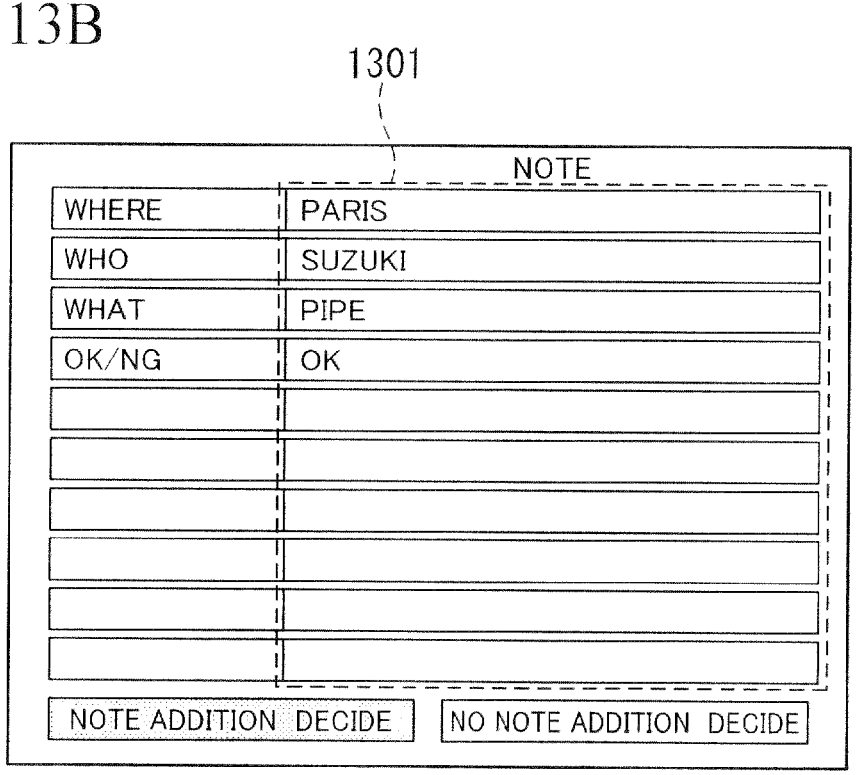

When a character input screen starts from the category column, the result of character input is reflected on the category column of the note edit screen. For example, when a character input screen (FIGS. 11A and 11B) starts in a state where a character string 'WHERE' of the category column 1000 shown in FIG. 10 is selected and a character string 'CITY' is input, the character string 'WHERE' of a category column 1300 is updated to 'CITY' as shown in FIG. 13A. Moreover, when a character input screen (FIGS. 12A and 12B) starts in a state where a character string 'NEW YORK' of the contents column 1001 shown in FIG. 10 is selected and a character string 'PARIS' is input, the character string 'NEW YORK' of a contents column 1301 is updated to 'PARIS' as shown in FIG. 13B. The user can input desired category and contents by repeating the above operation.

When the user operates a decision button 1310 by operation of the operation portion 14, character strings of the category and contents are fixed. When the operation of the decision button 1310 is detected, the main control portion 10 stores note data in a memory in the main control portion 10 and controls the recording medium reading and writing portion 15 to update the note data in the recording medium 16.

Figure 14:
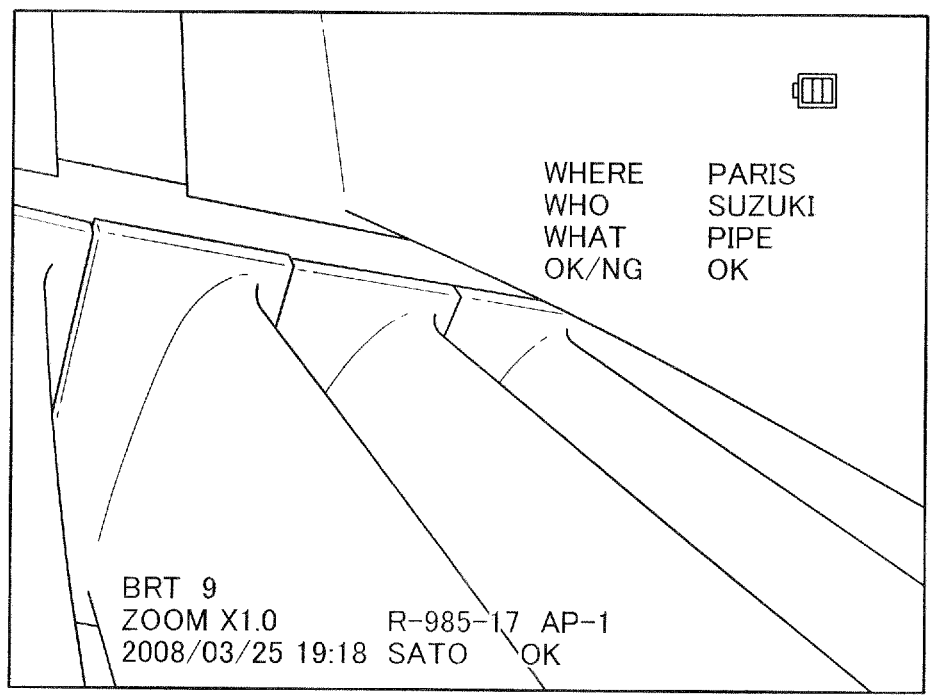
FIG. 14 is a reference view showing a screen after character input in an embodiment of the invention.

Then, when the user inputs an image recording instruction by operation of the operation portion 14, the main control portion 10 adds the note data stored in the memory (not shown) to image data output from the image processing portion 6 and outputs the result to the recording medium reading and writing portion 15. The recording medium reading and writing portion 15 writes and records the image data, to which note data is added, in the recording medium 16. The note data in the recorded image data may be displayed on an image viewer of a PC or the main body of the endoscope apparatus (FIG. 14).

Next, a third operation example will be described. In the third operation example, a favorite list is used in common in various operation modes. In addition, the frequency of use of a character string is recorded for every operation mode, and processing for changing the order of character strings displayed in the candidate column of the character input screen according to the frequency of use is executed. FIG. 16A shows the contents of a favorite list in the third operation example. A character string registered by the user is made to match the frequency of use for every operation mode. The frequency A of use is a frequency of use for the live mode, the frequency B of use is a frequency of use for the measurement mode, and the frequency C of use is a frequency of use for the play mode. A place, in which a character string is not registered, in the favorite list is an unused region (blank), and the frequency of use is set to 0.

When a character string not registered in the favorite list is newly registered in the favorite list, the character string is added in the unused region of the favorite list and '1' is set as the frequency of use for a running operation mode and 0 is set as the frequency of use for the other operation modes.

In addition, when a character string already registered in a favorite list (in other words, a character string that was used in one of operation modes) is used in one of operation modes, '1' is added to the frequency of use for the operation mode.

Figure 15:
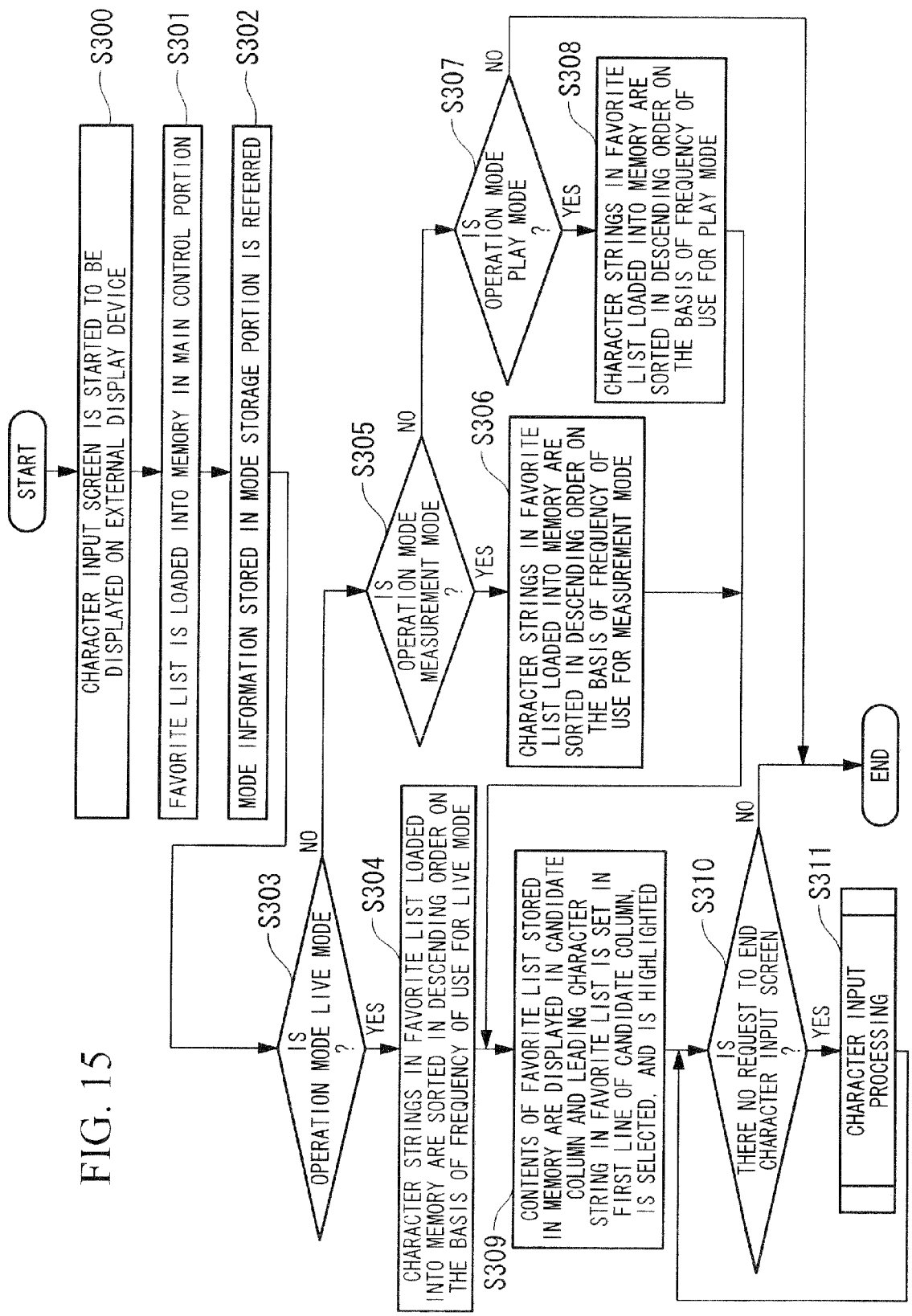
FIG. 15 is a flow chart showing the procedure of an operation of an endoscope apparatus according to an embodiment of the invention.

In the case of performing character input, the user operates the operation portion 14 to input a start instruction (display instruction) of a character input screen. The main control portion 10 detects the start instruction on the basis of a signal output from the operation portion 14. Subsequently, the main control portion 10 executes a control operation regarding character input according to the procedure shown in FIG. 15.

The main control portion 10 that has detected the start instruction instructs the graphic generating portion 13 to display the character input screen. The graphic generating portion 13 generates a graphic image signal for displaying the character input screen and outputs the graphic image signal to the image synthesizing portion 9. The image synthesizing portion 9 outputs the graphic image signal output from the graphic generating portion 13 to the external display device 8. The external display device 8 displays a character input screen on the basis of the graphic image signal (step S300).

Then, the main control portion 10 reads a favorite list from the favorite storage portion 18 and loads the favorite list into the memory in the main control portion 10 (step S301). Then, the main control portion 10 reads and refers to mode information stored in the mode storage portion 20 (step S302). When the mode information indicates the live mode (in the case of YES in step S303), the main control portion 10 sorts the character strings in the favorite list loaded into the memory in descending order on the basis of the frequency of use for the live mode (step S304).

Moreover, when the mode information indicates not the live mode but the measurement mode (in the case of NO in step S303 and YES in step S305), the main control portion 10 sorts the character strings in the favorite list loaded into the memory in descending order on the basis of the frequency of use for the measurement mode (step S306). In addition, when the mode information indicates the play mode other than the live mode and the measurement mode (in the case of NO in steps S303 and S305 and YES in step S307), the main control portion 10 sorts the character strings in the favorite list loaded into the memory in descending order on the basis of the frequency of use for the play mode (step S308). In addition, when the operation mode indicated by the mode information is none of the live mode, the measurement mode, and the play mode (in the case of NO in steps S303, S305, and S307), the control regarding the character input is ended.

When the character input screen starts in the live mode, the character strings in the favorite list shown in FIG. 16 are sorted on the basis of the frequency A of use for the live mode as shown in FIG. 17. Moreover, when the character input screen starts in the measurement mode, the character strings in the favorite list shown in FIG. 16 are sorted on the basis of the frequency B of use for the measurement mode as shown in FIG. 18. As described above, one page on which character strings can be simultaneously displayed in a character input screen are set in the unit of three lines from the head of the favorite list. That is, character strings from the head (first line) of the favorite list to a third line are set as a first page, character strings from a fourth line to a sixth line are set as a second page, and subsequent pages are similarly set in the unit of three lines. Accordingly, the priority of character strings related to display is determined by sorting the character strings in the favorite list in steps S304, S306, and S308.

Subsequent to steps S304, S306, and S308, the main control portion 10 controls the graphic generating portion 13 to generate a graphic image signal for displaying a character input screen including the character strings in the favorite list after sorting (step S309). As a result, the character input screens shown in FIGS. 5A and 5B and the like are started and the character strings on the first page in the favorite list are displayed in the candidate column.

Subsequent to step S309, the main control portion 10 determines whether or not there is a request to end the character input screen on the basis of a signal output from the operation portion 14 (step S310). If there is no end request (YES in step S310), the main control portion 10 executes character input processing (step S311). In addition, when there is an end request (NO in step S310), the main control portion 10 makes the character input screen not displayed, controls the graphic generating portion 13 to display the fixed character string, and ends the control regarding the character input.

Details of the character input processing in step S311 are the same as those in the first operation example. However, when a character string in the favorite list is selected and is displayed in the input column, the main control portion 10 updates the frequency of use of the character string, which corresponds to the operation mode indicated by the mode information among frequencies of use, by adding '1' to it.

As described above, by determining the priority of character strings on the basis of the frequency of use corresponding to an operation mode at the start of the character input screen, it becomes possible to display a frequently used character string at the start of the character input screen. As a result, since it becomes possible to preferentially input a character string which is optimal in each operation mode, an operation required for character input can be reduced.

Figure 19A:
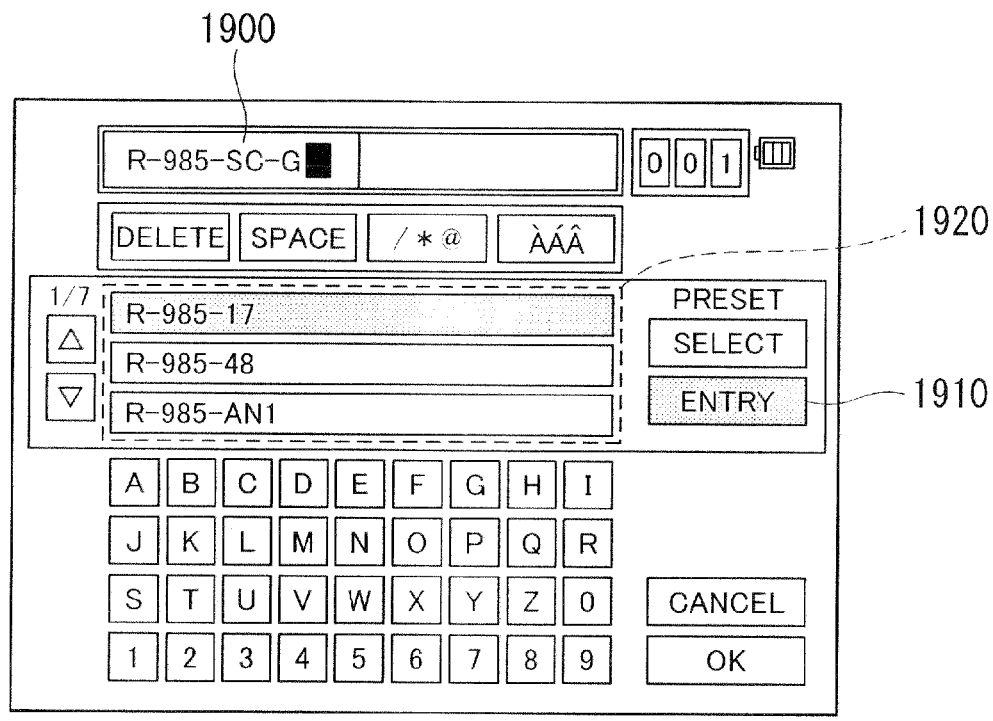
FIGS. 19A and 19B are reference views showing screens at the time of character input (at the time of favorite registration) in an embodiment of the invention.

Next, an operation in the case of registering a character string in a favorite list will be described. Similar to the above-described method, a user inputs a character string that the user wants to register by performing character input on a character input screen by operation of the operation portion 14. As shown in FIG. 19A, an input character string is displayed in an input column 1900. Then, when the user operates a favorite registration button 1910 by operation of the operation portion 14, the main control portion 10 controls the graphic generating portion 13 to display a registered character string in a current favorite list, which is stored in the favorite storage portion 18, in a candidate column 1920. When no character string is registered in the favorite list, the candidate column 1920 is in a blank state.

Figure 19B:
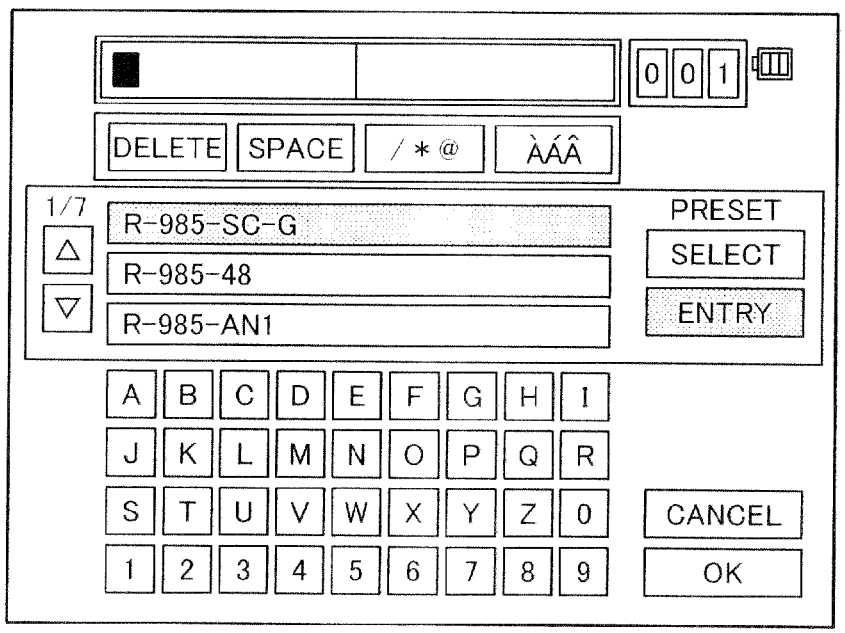

The user designates a line, in which the user wants to register a character string, by operation of the operation portion 14. FIG. 19A shows a state where a first line is selected. Then, the user performs an operation of registering a character string in the selected line by operation of the operation portion 14. The main control portion 10 that has detected the operation replaces the character string in the favorite list, which corresponds to the character string displayed in the first line of the candidate column 1920, with the character string displayed in the input column 1900 and stores the character string in the favorite storage portion 18. In addition, the main control portion 10 controls the graphic generating portion 13 to replace the character string displayed in the first line of the candidate column 1920 with the character string displayed in the input column 1900 and display it. As a result, as shown in FIG. 19B, the character string in the first line of the candidate column 1920 is updated. In addition, when a blank line is selected as a registration place of a character string, the character string that the user wants to register is displayed in the line and the character string is newly added in the favorite list.

In the case of registering a character string in a favorite list corresponding to the first and second operation examples, the main control portion 10 registers the character string in the favorite list corresponding to the operation mode indicated by the mode information stored in the mode storage portion 20. Moreover, in the case of registering a character string in a favorite list corresponding to the third operation example, the main control portion 10 sets the frequency of use for an operation mode, which is indicated by the mode information stored in the mode storage portion 20, to '1'.

In addition, when the favorite registration button 1910 is operated as described above and a line on the candidate column is designated in a state where the character string is not input to the input column 1900, it is possible to delete a character string in a favorite list corresponding to the line.

Next, a modification of the present embodiment will be described. By the following import and export functions, it is possible to share a favorite list with other apparatuses. In the case of outputting (exporting) a favorite list to another apparatus, the user inputs an instruction of export by operation of the operation portion 14. The main control portion 10 that has detected the instruction reads the favorite list from the favorite storage portion 18 and writes and records the favorite list in the recording medium 16 by control of the recording medium reading and writing portion 15.

In addition, in the case of inputting (importing) a favorite list created in another apparatus, the user inputs an instruction of import by operation of the operation portion 14. The main control portion 10 that has detected the instruction reads the favorite list from the recording medium 16 by control of the recording medium reading and writing portion 15 and writes the favorite list into the favorite storage portion 18.

In addition, not only transmission/reception of a favorite list to/from another apparatus may be performed through the recording medium 16, but also transmission/reception of the favorite list may be performed by connecting another apparatus as the external input device 12. Alternatively, transmission/reception of a favorite list to/from another apparatus may be performed by communication through a network.

In addition, the user may input a start instruction by operation of the screen start switch 17 instead of inputting a start instruction of a character input screen by operation of the operation portion 14. Alternatively, the user may input a start instruction by connecting the external input device 12.

In addition, it is also possible to provide a user login function for authenticating a user at the start of an endoscope apparatus, to prepare a favorite list for every user, and to switch the favorite list according to the login user. At this time, an icon or character string indicating the login user may be displayed on the character input screen.

As described above, according to the present embodiment, display/non-display of GUI components (for example, a candidate column and a button) for selecting a character string in a favorite list is controlled according to an operation mode of the apparatus. Specifically, in the first and second operation examples, GUI components for selecting a character string in a favorite list corresponding to the running operation mode are displayed. In the third operation example, GUI components for selecting a frequently used character string, which corresponds to the running operation mode, among character strings in a favorite list are displayed. As a result, since it becomes easy to select a character string suitable for each operation mode, time and effort for character input can be reduced.

In addition, the user can register a favorite character string in a favorite list of his or her own free will by storing the character string input by the user in the favorite list in the favorite storage portion 18.

In addition, the operability of character input can be improved by enabling input of a character string based on both a favorite input mode and a character button mode without switching a character input screen.

In an inspection using an endoscope apparatus, the inspector images a required place of a test subject while observing an image by inserting an insertion portion into the test subject. Furthermore, when a damaged part, the length and size of which should be checked, is formed in a test subject, it is necessary to measure the geometric feature of the test subject using a measurement function.

In the endoscopic inspection, images obtained by continuously imaging a test subject (imaging in series) are generally similar to each other. For example, when a pipe is a test subject and a plurality of images are obtained by imaging a plurality of places inside the pipe, just by glancing the plurality of images, the inspector can only understand that the images are images showing the inside of the pipe.

In order for the inspector to recognize easily and concretely to which place of the pipe the image corresponds, it is necessary to add explicit data to the image and to present (display) the explicit data to the inspector.

Therefore, if the inspector inputs characters for the image, the inspector can recognize easily and concretely to which place of the pipe the image corresponds when viewing the image later.

Figure 20:
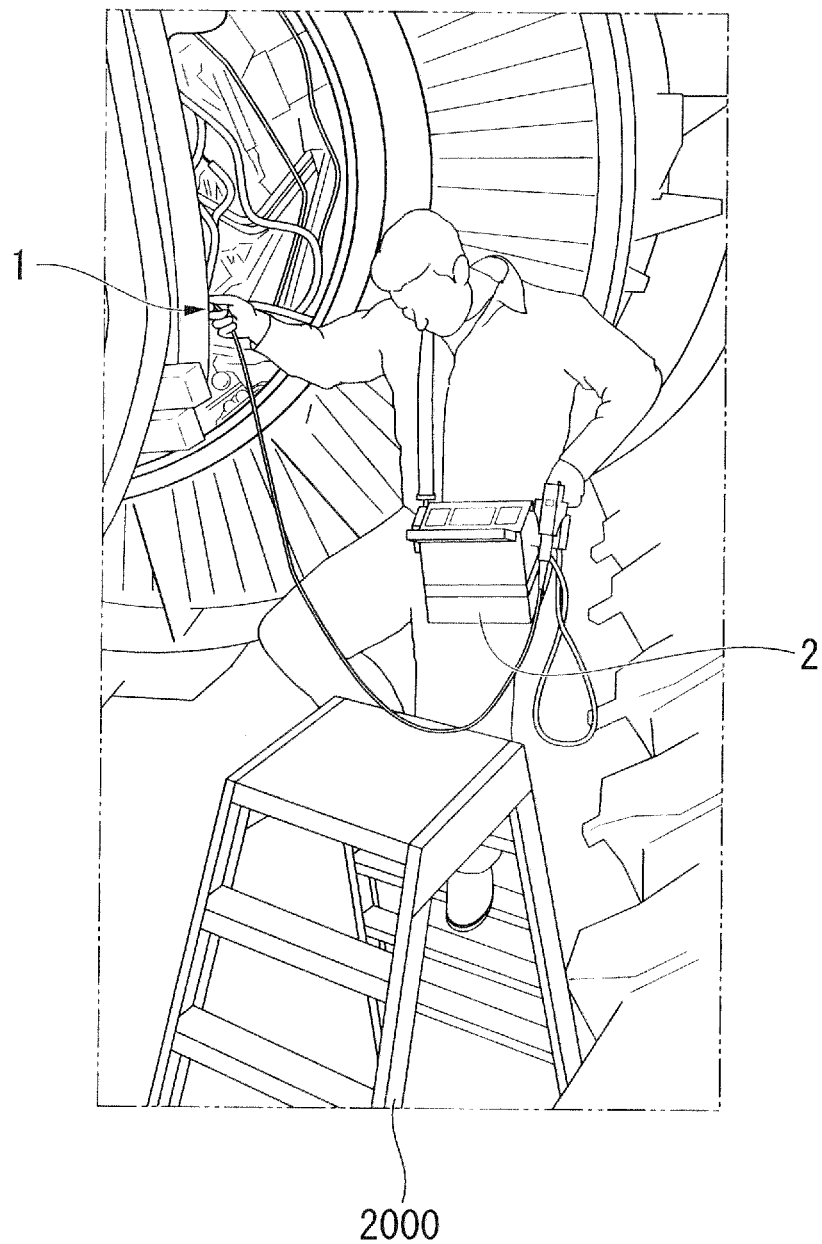
FIG. 20 is a reference view showing a state of an inspector at the time of endoscopic inspection using an industrial endoscope apparatus.

However, in the endoscopic inspection using an industrial endoscope apparatus, the inspector does not necessarily perform the inspection in satisfactory environment. For example, as shown in FIG. 20, there is a possibility that the inspector performs the inspection on an unstable stepladder 2000 or performs the inspection in an unstable condition (for example, a state where the inspector is raising one hand) in order to insert the insertion portion 1 into a test subject. In such an environment, for example, when the inspector images the test subject and inputs a character string to indicate the place and additionally performs measurement processing and inputs comments on the result as a character string and then resumes the inspection, it is preferable that the character input be performed in a short amount of time.

Accordingly, when the inspector performs character input, the inspector selects a character string in a favorite list recorded in the endoscope apparatus and the selected result is set as an input character string.

However, for example, in cases of comments on the inspection place and comments on the measurement result, the types of character strings to be input are different in many cases. For this reason, in the invention, character strings recorded in the endoscope apparatus are changed to character strings of a favorite list corresponding to an operation mode simultaneously with a change (for example, transition from the live mode to the measurement mode) of an operation mode.

In the invention, components for selection of a character string are selectively displayed according to an operation state (operation mode) of the apparatus. As a result, since a character string suitable for each operation state can be easily selected, the time and effort required for character input can be reduced.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope apparatus that is operable in a plurality of operation modes, the apparatus comprising:
    an endoscope that generates an image signal of a subject;
    an image signal processing portion that processes the image signal to generate image data;
    a display signal generating portion that generates a display signal for displaying an image based on the image data, and a character input screen;
    an operation portion that is operable to input a character via the character input screen;
    a character string storage portion that stores character strings such that the character strings are correlated with respective ones of the plurality of operation modes;
    a mode information storage portion that stores mode information corresponding to a currently-set operation mode to which the apparatus is currently set from among the plurality of operation modes in which the apparatus is operable;
    a reading portion that reads the stored mode information, which corresponds to the currently-set operation mode, from the mode information storage portion, and, in accordance with the read mode information, reads a character string, which corresponds to the currently-set operation mode corresponding to the read mode information, from the character string storage portion; and
    a control portion that (i) controls the display signal generating portion to display on the character input screen a component for selecting the character string read by the reading portion, (ii) controls the display signal generating portion to display the character string corresponding to the component when an operation of the component is detected, (iii) associates the character string selected via the character input screen with the image data, and (iv) records the image data and the selected character string in a recording medium.

2. The endoscope apparatus according to claim 1, wherein the character string storage portion stores the character strings and frequencies of use of the character strings for the respective operation modes of the apparatus such that the character strings are correlated to the frequencies of use thereof for the respective operation modes of the apparatus.

3. The endoscope apparatus according to claim 2, wherein the control portion controls display/non-display of the component based on the frequencies of use corresponding to the currently-set operation mode corresponding to the mode information stored in the mode information storage portion.

4. The endoscope apparatus according to claim 3, wherein, when the operation of the component is detected, the control portion updates the frequency of use of the character string corresponding to the component so as to correspond to the currently-set operation mode corresponding to the mode information stored in the mode information storage portion.

5. The endoscope apparatus according to claim 1, further comprising:
    a character string registration portion that stores a character string, which is input according to an operation of the operation portion, in the character string storage portion.

6. The endoscope apparatus according to claim 1, wherein the control portion controls the display signal generating portion to display a character string or an icon indicating the currently-set operation mode of the apparatus corresponding to the mode information stored in the mode information storage portion.

7. The endoscope apparatus according to claim 1, wherein the character string storage portion is separate from an image data storage portion for storing the generated image data.

8. The endoscope apparatus according to claim 1, wherein the character string storage portion stores the character strings without associating the character strings with the generated image data.

9. A method of displaying a character string for an endoscope apparatus that is operable in a plurality of operation modes, the apparatus including an endoscope that generates an image signal of a subject, an image signal processing portion that processes the image signal to generate image data, a display signal generating portion that generates a display signal for displaying an image based on the image data and a character input screen, and an operation portion that is operable to input a character via the character input screen, the method comprising:

storing character strings such that the character strings are correlated with respective ones of the plurality of operation modes;

storing mode information corresponding to a currently-set operation mode to which the apparatus is currently set from among the plurality of operation modes in which the apparatus is operable;

reading the stored mode information, which corresponds to the currently-set operation mode, and reading, in accordance with the read mode information, a character string, which corresponds to the currently-set operation mode corresponding to the read mode information, from among the stored character strings;

controlling the display signal generating portion to display on the character input screen a component for selecting the read character string;

when an operation of the component is detected, controlling the display signal generating portion to display the character string corresponding to the component;

associating the character string selected via the character input screen with the image data; and recording the image data and the selected character string in a recording medium.

10. The method of displaying a character string according to claim 9, wherein, in the storing of the character string, character strings and frequencies of use of the character strings for the respective operation modes of the apparatus are stored such that the character strings are correlated to the frequencies of use thereof for the respective operation modes of the apparatus.

11. The method of displaying a character string according to claim 10, wherein, in the displaying of the character input screen, display/non-display of the component is controlled based on the frequencies of use corresponding to the currently-set operation mode corresponding to the stored mode information.

12. The method of displaying a character string according to claim 11, wherein, in the displaying of the character string, when the operation of the component is detected, the frequency of use of the character string corresponding to the component is updated so as to correspond to the currently-set operation mode corresponding to the stored mode information.

13. The method of displaying a character string according to claim 9, wherein, in the storing of the character string, the character strings are input according to an operation of the operation portion.

14. The method of displaying a character string according to claim 9, wherein, in the displaying of the character input screen, the display signal generating portion is controlled to display a character string or an icon indicating the currently-set operation mode corresponding to the stored mode information.

15. The method of displaying a character string according to claim 9, wherein:

in the displaying of the character input screen, character buttons as components for selecting a character are displayed on the character input screen; and in the displaying of the character string, when an operation of a character button is detected, a character corresponding to the character button is displayed.

16. The method of displaying a character string according to claim 15, wherein, in the displaying of the character string, when an operation of a character button is detected, a word dictionary is read from a storage portion and a plurality of candidates for character conversion corresponding to the selected character are searched for.

17. The method of displaying a character string according to claim 16, wherein, in the displaying of the character string, when the character input using the component for selecting the read character string and the character input using the character buttons is performed continuously, the display signal generating portion is controlled such that the read character string and a character selected by using the character button are displayed in combination.

18. The method of displaying a character string according to claim 15, wherein, in the displaying of the character string, switching is performed between character input using the component for selecting the read character string and character input using the character buttons.

19. The method of displaying a character string according to claim 9, wherein the storing of the character strings comprises storing the character strings in a character string storage portion which is separate from an image data storage portion for storing the generated image data.

20. The method of displaying a character string according to claim 9, wherein the storing of the character strings comprises storing the character strings without associating the character strings with the generated image data.

* * * * *